(12) United States Patent
Sum et al.

(10) Patent No.: US 11,667,946 B2
(45) Date of Patent: Jun. 6, 2023

(54) DETECTION OF BETA-HEMOLYTIC PATHOGENS

(71) Applicant: TEMASEK LIFE SCIENCES LABORATORY LIMITED, Singapore (SG)

(72) Inventors: Rongji Sum, Singapore (SG); Muthukaruppan Swaminathan, Singapore (SG); Ian Cheong, Singapore (SG)

(73) Assignee: Temasek Life Sciences Laboratory Limited, Singapore (SG)

(*) Notice: Subject to any disclaimer, the term of this patent is extended or adjusted under 35 U.S.C. 154(b) by 369 days.

(21) Appl. No.: 17/077,581

(22) Filed: Oct. 22, 2020

(65) Prior Publication Data
US 2021/0108246 A1    Apr. 15, 2021

Related U.S. Application Data

(62) Division of application No. 16/079,270, filed as application No. PCT/SG2017/050081 on Feb. 23, 2017, now Pat. No. 10,844,418.

(60) Provisional application No. 62/300,372, filed on Feb. 26, 2016.

(51) Int. Cl.
C12Q 1/04      (2006.01)
C12Q 1/10      (2006.01)
C12Q 1/14      (2006.01)

(52) U.S. Cl.
CPC ............ *C12Q 1/04* (2013.01); *C12Q 1/10* (2013.01); *C12Q 1/14* (2013.01)

(58) Field of Classification Search
CPC ............ C12Q 1/04; C12Q 1/10; C12Q 1/14
See application file for complete search history.

(56) References Cited

U.S. PATENT DOCUMENTS

2010/0331211 A1    12/2010    Mosticone et al.

FOREIGN PATENT DOCUMENTS

EP        3420099 B1        4/2021

OTHER PUBLICATIONS

International Search Report and Written Opinion issued in Application No. PCT/SG2017/050081 dated Apr. 24, 2017, 14 pages.
Susan Bingaman et al. "Liposomal preparation for the in vivo monitoring of osmolality", The FASEB Journal, vol. 22, supplement, p. 927.4, Published online Mar. 1, 2008, 1 page.
N.T. Thet et al. "Visible colorimetric dissemination between pathogenic strains of Staphylococus aureus and Pseudomonas aeruginosa using fluorescent dye containing lipid vesicles", Biosensors and Bioelectronics, 2013, vol. 41, pp. 538-543.
Tatsuji Yasuda et al. "A simple method to measure anti-glycolipid antibody by using complement-mediated immune lysis of fluorescent dye-trapped liposomes", Journal of Immunological Methods, 1981, vol. 44, pp. 153-158.
Mats Silvander et al. "Effects of PEG-lipids on permeability of phosphatidylcholine/cholesterol liposomes in buffer and in human serum", Chemistry and physics of Lipids, 1998, vol. 97, pp. 15-26.
Gianfranco Pasut et al. "Polyethylene glycol (PEG)-dendron phospholipids as innovative constructs for the preparation of super stealth liposomes for anticancer therapy", Journal of Controlled Release, 2015, vol. 199, pp. 106-113.
European Office Action issued for Eurpean Patent Application No. 17756931.6 dated Dec. 13, 2019, 7 pages.
Johnsson et al., "Phase Behavior and Aggregate Structure in Mixtures of Dioleoylphosphatidylethanolamine and Poly (Ethylene Glycol)-Lipids" Biophysical Journal. Jan. 2001, vol. 80, pp. 313-323.
The European Communication with a supplementary European Search Report issued in Application No. 17756931.6 dated Dec. 11, 2018, 9 pages.
Zhou, Jin et al. "Development of a prototype wound dressing technology which can detect and report colonization by pathogenic bacteria", Biosensors and Bioelectronics, Elsevier Science Ltd. UK, Amsterdam, NL, vol. 30, No. 1, Aug. 22, 2011, pp. 67-72, XP028334465.
Marshall, Serena E. et al. "Effect of Lipid and Fatty Acid Composition of Phospholipid Vesicles on Long-Term Stability and Their Response to Staphylococcus aureus and Pseudomonas aeruginosa Supernatants", Langmuir, vol. 29, No. 23, May 28, 2013, pp. 6989-6995, XP055522644.
First Examination Report issued in corresponding Indian Application 17/077,581, dated Jun. 16, 2021, 6 pages.
G. Haran et al. "Transmembrane ammonium sulfate gradients in liposomes produce efficient and stable entrapment of amphipathic weak bases", Biochimica et Biophysica Acta (BBA)-Biomembranes, 1151(2), Sep. 19, 1993, pp. 201-215.
I. Cheong et al., A Bacterial Protein Enhances the Release and Efficacy of Liposomal Cancer Drugs. Science, 314(5803), Nov. 24, 2006, pp. 1308-1311.
Chinese Office Action issued in corresponding Chinese Application No. 201780025857.0, dated Jun. 3, 2021, 18 pages (with English Translation).

*Primary Examiner* — Satyendra K Singh
(74) *Attorney, Agent, or Firm* — Rothwell, Figg, Ernst & Manbeck, P C.

(57) ABSTRACT

The present invention relates to the field of diagnostics and more particularly to the detection of beta-hemolytic pathogens. More specifically, the present invention relates to the rapid and accurate detection of beta-hemolytic pathogens using sterically-stabilized liposomes.

14 Claims, 14 Drawing Sheets

Fig. 4A
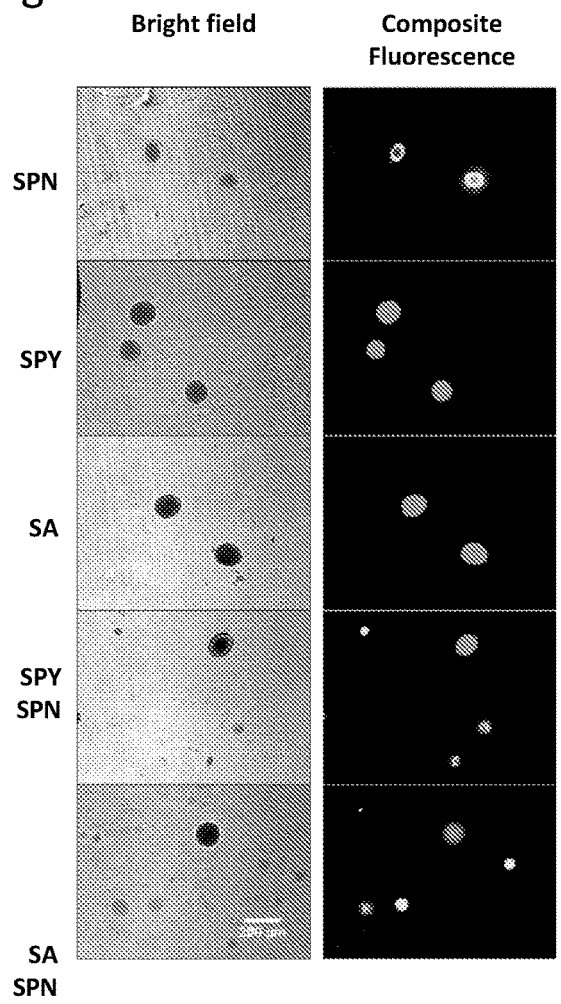
Fig. 4B
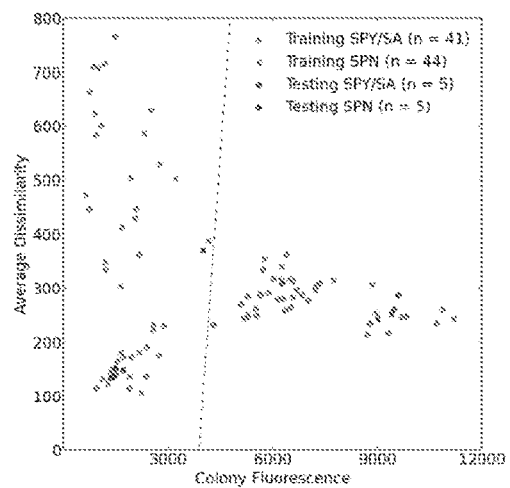
Fig. 4C
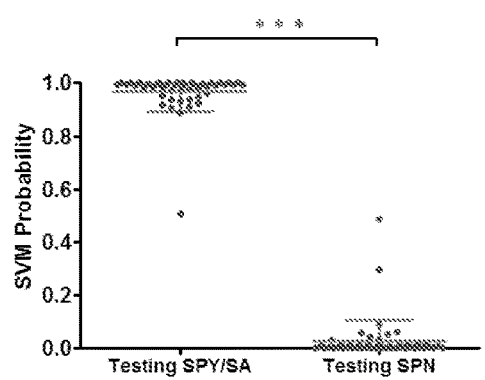
Fig. 4D
| Total colonies | 95 |
| --- | --- |
| Cross Validation | 10-fold |
| Accuracy | 99% |
| Sensitivity | 98% |
| Specificity | 100% |

Fig. 11A

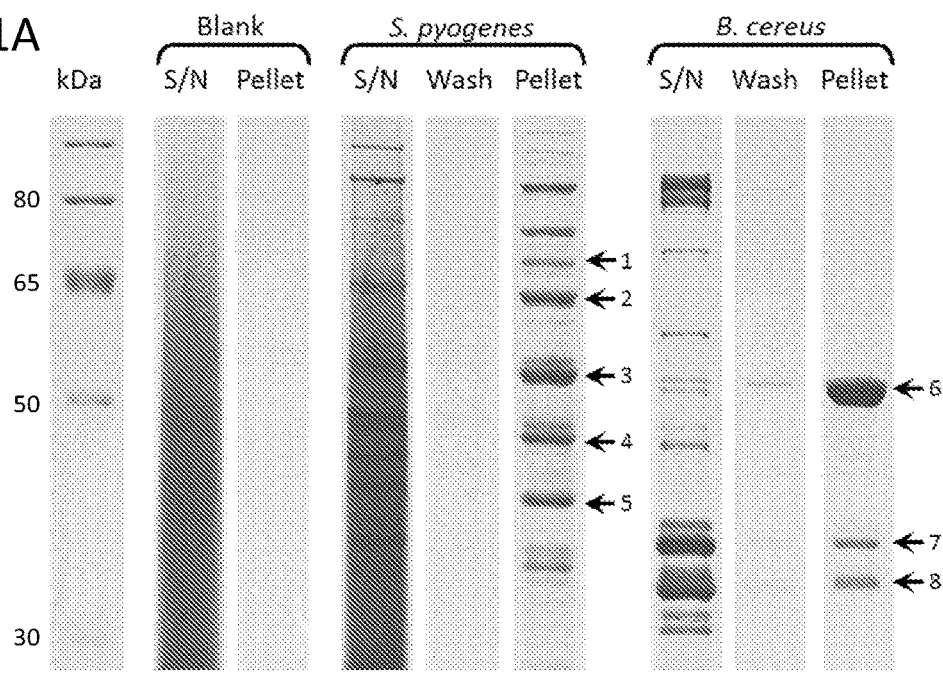

Fig. 11B

| Bacterium | Protein | Gene Name | Accession number | Band | MW (KDa) |
|---|---|---|---|---|---|
| Streptococcus pyogenes | Oligopeptide binding protein | SarA | V6WCL3_STRPY | 1 | 72.1 |
| | Streptolysin O | Slo | Q1JNR8_STRPC | 2 | 64.1 |
| | ATP synthase alpha subunit | AtpA | V6W8K9_STRPY | 3 | 54.7 |
| | Elongation factor Tu | Tuf | U9X001_STRPY | 4 | 46.0 |
| | Putative secreted protein | Spy49_0015 | B5XJ10_STRPZ | 5 | 41.8 |
| Bacillus cereus | Alveolysin | bcere0028_15310 | A0A063CJ80_BACCE | 6 | 56.7 |
| | Haemolytic Enterotoxin | Hbl | C2QRL8_BACCE | 7 | 43.6 |
| | Enterotoxin B | NheB | Q9S3N3_BACCE | 8 | 36.9 |

Fig. 12

| P-value / CFUs | <0.001 | <0.005 | <0.01 | <0.05 |
|---|---|---|---|---|
| $10^4$ | 64 | 36 | 28 | 18 |
| $10^3$ | 194 | 167 | 160 | 150 |
| $10^2$ | 324 | 298 | 292 | 282 |
| $10^1$ | 454 | 429 | 424 | 414 |
| $10^0$ | 584 | 560 | 556 | 546 |

DETECTION OF BETA-HEMOLYTIC PATHOGENS

CROSS-REFERENCE TO RELATED APPLICATIONS

The present application is a division of U.S. patent application Ser. No. 16/079,270, filed 23 Aug. 2018, now U.S. Pat. No. 10,844,418, which is a national stage filing under 35 U.S.C. § 371 of PCT/SG2017/050081, filed on 23 Feb. 2017, which is related to and claims the benefit of U.S. Provisional Patent Application Ser. No. 62/300,372 filed on 26 Feb. 2016. Each application is incorporated by reference herein in its entirety.

BACKGROUND OF THE INVENTION

The present invention relates to the field of diagnostics and more particularly to the detection of beta-hemolytic pathogens. More specifically, the present invention relates to the rapid and accurate detection of beta-hemolytic pathogens using sterically-stabilized liposomes.

The publications and other materials used herein to illuminate the background of the invention, and in particular, cases to provide additional details respecting the practice, are incorporated by reference, and for convenience are referenced in the following text by number and are listed by number in the appended bibliography.

It is well known that beta-hemolytic microorganisms are pathogenic as a general rule and causative of a wide spectrum of animal diseases. Common examples include *Streptococcus pyogenes* (pharyngitis), *Listeria monocytogenes* (Listeriosis), *Clostridium perfringens* (Gas gangrene), *Clostridium novyi* (Black sheep disease), *Staphylococcus aureus* (general infections) and *Bacillus cereus* (food poisoning). Because no known non-pathogenic bacteria are also beta-hemolytic, beta-hemolysis has a high positive predictive value for the detection of bacterial pathogens. Consequently, a test for beta-hemolysis with few, if any, false positive is informative.

It is for this reason that the Red Blood Cell (RBC) agar plate, invented in 1903, is still the gold standard for identifying beta-hemolysis. However, RBC agar cultures suffer from one major flaw. Their results take too long to be clinically relevant in most situations. The reason for the lengthy incubation period is that bacterial colonies must create a visible clearing through the opaque RBCs. However, to achieve this visual result, colonies must secrete a significant quantity of hemolysin which means that the colonies must grow to a relatively large size. Two examples illustrate the consequence of this problem. Only 5-10% of sore throat infections are caused by bacteria, with Group A beta-hemolytic streptococci being the most common cause [1]. However, blood agar is unable to identify beta-hemolysis within a time frame which would allow clinicians to decide if antibiotic treatment is appropriate. For this reason, current testing is based on antigen detection kits which are quick but insensitive in comparison to blood agar cultures. The second example is food safety monitoring. The lack of on-site rapid testing for bacterial pathogens cripples the ability of food companies to respond to bacterial contamination of their food products. In both scenarios, a rapid functional test for beta-hemolysis would provide accurate and timely information for decision making.

Although there are no commercially available rapid diagnostic tests for beta-hemolysis, such tests do in fact exist for the detection of particular beta-hemolytic species. These approaches are based on the detection of genetic or antigenic determinants and not beta-hemolysis. Examples include the rapid antigen detection tests for Group A Streptococci [2,3] and nucleic acid-based assays for specific genes or ribosomal RNA [4, 5]. These methods are useful for identifying specific bacteria with a quick turnaround time but they are insensitive and unreliable when the pathogen is a single cell. Further, centralized testing facilities are required to execute these methods. These limitations underscore the need for a broad assay that will not only detect beta-hemolysis but also outperform RBC agar in speed and scalability.

Recently, alternative tests have been developed. One example is described in Korean patent application publication No. KR 10-2007-0042294. This test is designed for selectively detecting hemolytic bacteria such as *Listeria monocytogenes*, *Listeria welshimeri*, *Staphylococcus aureus* and *Escherichia coli* H5 0157. The test detects a signal of a specific microorganism in a method that uses liposomes which include a microorganism specific detection reagent, such as chromogenic reagents and electrochemical-based analytical reagents. A biosensor is used for selectively detecting hemolytic bacteria and comprises a standard microorganism, a liposome including a microorganism specific detection reagent, a signal measuring machine, various reaction solutions and buffer solutions. Although this test is rapid and sensitive, it has the disadvantages that it uses a blood agar medium and that it is not negative for alpha- and gamma-hemolytic bacteria, i.e., that the test is specific for beta-hemolytic bacteria with no, if any, false positives resulting from alpha- and gamma-hemolytic bacteria.

Another example is described in U.S. patent application publication No. US 2010/0331211 which describes a method for detecting at least one target microorganism that may be present in a sample. The method includes the steps of: (a) bringing into contact, in a container, the sample, a medium that enables the growth of the target microorganism(s), and a cell population (such as red blood cells or liposomes) capable of being lysed by the target microorganism(s); (b) subjecting the whole to a temperature that promotes the growth of the target microorganism(s); and (c) observing, in real time, lysis of the cell population, e.g. by measuring the disappearance of fluorescence or appearance of color, indicating the presence of the target microorganism(s). Although this test is sufficiently rapid, it has the disadvantages that it may use a blood agar medium and that it is not negative for alpha- and gamma-hemolytic bacteria.

Additionally, the hemolysis of lipid vesicles or liposomes has been described for distinguishing *S. aureus* from *Pseudomonas aeruginosa* in a biosensing test. See Thet et al., *Biosens Bioelectron* 41:538-544, 2013. However, these lipid vesicles were specifically designed for this test and there is no disclosure that they would be useful for detecting beta-hemolytic pathogens and that the test is not negative for alpha- and gamma-hemolytic bacteria. An electrochemical sensor test based on the hemolytic actions toward liposome is described by Kim et al., *Sensors and Actuators B: Chemical* 119:143-149, 2006. This test uses liposomes and the mediator 2,6-dichlorophenolindophenol and shows selectivity toward hemolytic bacteria, including *Listeria monocytogenes*. There is no disclosure that the test is not negative for alpha- and gamma-hemolytic bacteria. A chromatic detection test is described by Silbert et al., *Appl Environ Microbiol* 72:7339-7344, 2006. This test uses agar-embedded nanoparticles comprising phospholipids and the chromatic polymer polydiacetylene and can identify gram-negative and gram-positive bacteria. There is no disclosure that they would be useful for detecting beta-hemolytic pathogens and that the test is not negative for alpha- and gamma-hemolytic bacteria.

It is desired to develop a method for rapid, reliable and generic detection of beta-hemolytic pathogens that is specific for the beta-hemolytic pathogens with little or no false positives that can be caused by alpha- and gamma-hemolytic pathogens.

SUMMARY OF THE INVENTION

The present invention relates to the field of diagnostics and more particularly to the detection of beta-hemolytic pathogens. More specifically, the present invention relates to the rapid and accurate detection of beta-hemolytic pathogens using sterically-stabilized liposomes.

The present invention provides a method for detecting the presence of beta-hemolytic pathogens in a sample. The method comprises: (a) adding a sample suspected of containing a beta-hemolytic pathogen to a growth medium containing sterically-stabilized liposomes comprising an encapsulated fluorophore to form a test assay mixture; (b) incubating the test assay mixture for a period of time sufficient for the beta-hemolytic pathogen, if present, to form a population of test cells and to cause lysis of the sterically-stabilized liposomes to release the fluorophore into the assay mixture for assimilation into the population of test cells; (c) detecting the fluorescence of the population of test cells; and (d) comparing the amount of fluorescence of the population of test cells with the amount of fluorescence of a population of control cells.

In some embodiments, the fluorophore is a DNA-binding dye that can associate with pathogens. In some embodiments, the fluorophore is assimilated by beta-hemolytic pathogens which fluoresce. In some embodiments, the fluorophore is selected on the basis of the pathogens' permeability to the fluorophore. In one embodiment, the fluorophore is assimilated by gram-positive bacteria. In another embodiment, the fluorophore is assimilated by gram-negative bacteria. In some embodiments, the fluorophore is a non-membrane permeable fluorescent dye which is able to exhibit self-quenching. In other embodiments, the fluorophore is selected on the basis of the background fluorescence of the growth medium. In some embodiments, the growth medium is a solid medium and the population of test cells form one or more test colonies. In one embodiment, the solid medium is agar-based. In other embodiments, the growth medium is a liquid medium. In some embodiments, the sterically-stabilized liposomes are liposomes stabilized by polyethylene glycol (PEG). In one embodiment, the PEG is PEG2000. In some embodiments, the sterically-stabilized liposomes are lysed by beta-hemolytic pathogens, but not by alpha- and gamma-hemolytic pathogens. In other embodiments, the pathogens are bacteria.

In one embodiment, the present invention provides a method for detecting the presence of beta-hemolytic pathogens in a sample using a solid growth medium. In some embodiments, this method comprises: (a) adding a sample suspected of containing a beta-hemolytic pathogen to a solid growth medium containing sterically-stabilized liposomes comprising an encapsulated fluorophore to form an assay mixture; (b) incubating the assay mixture for a period of time sufficient for the beta-hemolytic pathogen, if present, to form one or more test colonies and to cause lysis of the sterically-stabilized liposomes to release the fluorophore into the assay mixture for assimilation into the one or more test colonies; (c) detecting the fluorescence of the one or more test colonies; and (d) comparing the amount of fluorescence of the one or more test colonies with the amount of fluorescence of one or more control colonies. In other embodiments, the method further comprises quantitating a textural component of the colony fluorescence of the one or more test colonies and the background fluorescence associated with the one or more control colonies.

In some embodiments, the fluorophore is a DNA-binding dye that can associate with pathogens. In some embodiments, the fluorophore is assimilated by beta-hemolytic pathogens which fluoresce. In some embodiments, the fluorophore is selected on the basis of the pathogens' permeability to the fluorophore. In one embodiment, the fluorophore is assimilated by gram-positive bacteria. In another embodiment, the fluorophore is assimilated by gram-negative bacteria. In other embodiments, the fluorophore is selected on the basis of the background fluorescence of the growth medium. In some embodiments, the solid medium is an agar-based solid medium. In other embodiments, the sterically-stabilized liposomes are liposomes stabilized by polyethylene glycol (PEG). In one embodiment, the PEG is PEG2000. In some embodiments, the sterically-stabilized liposomes are lysed by beta-hemolytic pathogens, but not by alpha- and gamma-hemolytic pathogens. In other embodiments, the pathogens are bacteria.

In another embodiment, the present invention provides a method for detecting the presence of beta-hemolytic pathogens in a sample using liquid growth medium. In some embodiments, this method comprises: (a) adding a sample suspected of containing a beta-hemolytic pathogen to a liquid growth medium containing sterically-stabilized liposomes comprising an encapsulated fluorophore to form an assay mixture; (b) incubating the assay mixture for a period of time sufficient for the beta-hemolytic pathogen, if present, to form a population of test cells and to cause lysis of the sterically-stabilized liposomes to release the fluorophore into the assay mixture for assimilation into the population of test cells; (c) detecting the fluorescence of the population of test cells; and (d) comparing the amount of fluorescence of the population of test cells with the amount of fluorescence of a population of control cells. In other embodiments, the method further comprises determining the Time-To-Detection (TTD). TTD is defined as the point when fluorescence of a time-series significantly exceeds that of *S. pneumoniae* at $p<0.005$.

In some embodiments, the fluorophore is a DNA-binding dye that can associate with pathogens. In some embodiments, the fluorophore is assimilated by beta-hemolytic pathogens which fluoresce. In some embodiments, the fluorophore is selected on the basis of the pathogens' permeability to the fluorophore. In one embodiment, the fluorophore is assimilated by gram-positive bacteria. In another embodiment, the fluorophore is assimilated by gram-negative bacteria. In some embodiments, the fluorophore is a non-membrane permeable fluorescent dye which is able to exhibit self-quenching. In other embodiments, the fluorophore is selected on the basis of the background fluorescence of the growth medium. In other embodiments, the sterically-stabilized liposomes are liposomes stabilized by polyethylene glycol (PEG). In one embodiment, the PEG is PEG2000. In some embodiments, the sterically-stabilized liposomes are lysed by beta-hemolytic pathogens, but not by alpha- and gamma-hemolytic pathogens. In other embodiments, the pathogens are bacteria.

The present invention also provides a kit for conducting methods or assays described herein for detecting beta-hemolytic pathogens. In some embodiments, the kit comprises sterically-stabilized liposomes and a fluorophore. In some embodiments the fluorophore is encapsulated in the liposomes. In other embodiments, the fluorophore is separate from the liposomes and encapsulated into the liposomes prior to use. In some embodiments, the kit further comprises a growth medium. In some embodiments, the growth medium is a solid medium. In other embodiments, the growth medium is a liquid medium. In some embodiments, the kit also comprises a control pathogen. In some embodiments, the kit further comprises instructions for carrying out the method or assay.

The present invention also provides for use of sterically-stabilized liposomes comprising an encapsulated fluorophore described herein for the detection of beta-hemolytic pathogens. In some embodiments, the pathogen is a bacteria. The present invention further provides for the use of a kit described herein for the detection of beta-hemolytic pathogens. In some embodiments, the pathogen is a bacteria.

BRIEF DESCRIPTION OF THE FIGURES

FIG. 1A: Beta-hemolytic colonies in Brain Heart Infusion (BHI) agar media with L-Hoechst fluoresce intensely after overnight incubation. In comparison, alpha and gamma-hemolytic colonies showed little to no visible fluorescence.

FIG. 1B: Reported colony fluorescence values are normalized to background fluorescence. The average fluorescence of each beta-hemolytic bacterium is significantly higher than that of LL, the control bacterium with the highest fluorescence (P<0.0001). FIG. 1C: Relative dimensions of a red blood cell, a bacterial rod and a liposome are shown. FIG. 1D: SPY and BC colony fluorescence levels become visible just hours after plating in BHI agar and exponentially increase, reaching high levels in less than 24 hours. SE and EC fluorescence remains low. FIG. 1E: Beta and non-beta hemolytic bacteria can be linearly separated by the intensity (Colony Fluorescence) and texture (Average Dissimilarity) of L-Hoechst staining using support vector machines (SVM) as the classifier. Scale bars, 50 μm. Error bars, means±s.d. *** P<0.0001.

FIG. 3A: Gram-positive colonies (BC, SPY, SA, CP, LM, SS, SO, SE, LL, XL1) are able to take up free H33342 dye after overnight incubation with BHI agar supplemented with H33342. Gram-positive cells take up the dye better than EC. FIG. 3B: L-H33342 (which incorporates DSPE-PEG$_{2000}$) is stable in BHI with Fetal Bovine Serum (final concentration, 10%) over 24 hours, with basal leakage of 1.4%. FIG. 3C: Sodium hexametaphosphate, a membrane permeabilizer increases the fluorescence uptake of EC although at 0.3% it is lethal to SPY. Experiments were repeated thrice. Error bar summaries of the data are means±s.d. ***P<0.0001.

FIGS. 4A-4D show that beta-hemolytic colonies are distinguishable in agar co-cultures with alpha hemolytic SPN. FIG. 4A: SA and SPY were each co-incubated overnight with SPN in BHI agar+L-Hoechst. Individual cultures of SA, SPY and SPN served as controls. Colonies which lyse L-Hoechst fluoresce blue but are artificially shown here as red for contrast. SPN colonies were labelled with green fluorescence by immunostaining the agar matrix with antibodies specific for SPN. Brightfield images help to locate colony positions. Beta-hemolytic colonies can be positively identified using L-Hoechst, even when in close proximity to non-beta hemolytic SPN colonies. FIG. 4B: Using the lack or presence of green fluorescence as ground truth for identifying SPY/SA (n=46) versus SPN (n=49) colonies, both colony classes were randomly partitioned into training and testing sets. The training set was used to establish an SVM computed 1-dimensional hyperplane (shown as a dotted line) to separate the classes based on colony fluorescence and average dissimilarity of L-Hoechst staining. The testing set was used to validate the accuracy of the trained SVM classifier. In this typical example, classification accuracy is 100%. FIG. 4C: The experiment in (b) was repeated using a 10-fold cross validation framework. Mean SVM probabilities (the probability of beta-hemolysis) and standard deviations are reported. SPY/SA is significantly different from SPN (P<0.0001). FIG. 4D: Summary SVM classification results from (c) are shown in tabular form. Error bars, means±s.d. ***P<0.0001.

FIGS. 5A-5G: A panel of bacteria (BC, SPY, SA, CP, LM, SPN, SS, SE and EC) were inoculated in 384-well plates containing BHI broth, Fetal Bovine Serum and L-SRB. All exponents stated in the legends refer to the inoculum size in CFUs. Beta-hemolytic bacteria were observed to lyse L-SRB and cause a sharp increase in SRB fluorescence reported as % Lysis. In contrast, alpha-hemolytic (SPN and SS) and gamma-hemolytic (SE and DH5) bacteria did not show an appreciable increase in signal despite turbid growth (FIGS. 6A-6D; FIG. 5B: A rescaled version of (a) is shown. Time-to-Detection (TTD) for each SPY time-series (P<0.005) is marked by an *. TTD increases monotonically with inoculum size. FIG. 5H: Consolidated TTDs for all beta-hemolytic bacteria tested correlate linearly ($R^2$>0.96) with inoculum size (log CFUs). Error bars, means±s.d.

FIGS. 6A-6D: Growth curves of (a) SPY, (b) CP, (c) SA and (d) LM measured by OD$_{600}$ over 15 hours show turbid growth for all inoculum sizes. SPN, SS, SE and EC are plotted on the same graphs for reference. Larger inocula correlate with earlier entry into exponential growth. SPN cells exhibit a typical lag and exponential phases but autolyzes at stationary phase, leading to a dip in its growth curve. Experiments were repeated thrice. Error bar summaries of the data are means±s.d.

FIGS. 7A-7D BC show mediated lysis of L-SRB. FIG. 7A: % Lysis of L-SRB by BC cells inoculated from a live culture is shown here. Lysis kinetics are similar to that of BC cells inoculated from a frozen bacterial stock. FIG. 7B: The TTD for BC was only slightly affected by deep freezing of cells at limiting dilutions of a single CFU and below. FIGS. 7C and 7D: Growth curves of live and frozen BC cells measured by $OD_{600}$ show turbid growth for all inoculum sizes. Experiments were repeated thrice. Error bar summaries of the data are means±SD.

FIG. 8A: Lysis of L-SRB at the 12-hour endpoint was unaffected by SPN at BC inoculums above $10^0$. FIG. 8B: The time to detection of BC in admixtures with SPN was only affected at limiting dilutions of BC, but not if there were at least 10 CFUs of BC. FIGS. 8C and 8D: The kinetics of BC lysis of L-SRB in the presence-(c) or absence-(d) of SPN was plotted for varying CFUs of BC. Kinetics is comparable between the two conditions when there were at least 10 CFUs of BC. Error bars, means±s.d.

FIG. 9 shows broth co-cultures of BC and SPN over 12 hours. Growth curves of serially diluted BC inocula admixed with a constant $10^4$ CFUs of SPN are shown. All exponents stated in the legends refer to the inoculum size in CFUs. The growth curves of high BC inocula (≥$10^2$ CFUs) were not affected by SPN. These admixture samples were similar to BC only curves. The combination of $10^1$ CFUs of BC and $10^4$ CFUs of SPN exhibits a biphasic growth phase. The dip at 400 minutes followed by recovery at 600 minutes are likely to be driven by SPN autolysis and BC growth respectively. Limiting dilutions of BC ($10^{-1}$ CFUs) result in a curve similar to SPN alone. Experiments were repeated thrice. Error bar summaries of the data are means±s.d.

FIG. 10 shows visualization of SPN in admixtures with BC by immunofluorescence. After the co-culture of BC and SPN described in FIG. 9, these broth co-cultures were diluted to a standard optical density and stained with an antibody specific for SPN. Few or no SPN cells were observed within the range of $10^6$ to $10^4$ CFUs of BC. The proportion of green fluorescent SPN cells increases as an inverse proportion of BC inoculum size. Microscope images were representative images from three experiments. Scale bar, 5 μm.

FIGS. 11A and 11B show that L-SRB interacting proteins from BC and SPY are isolated and identified. FIG. 11A: Overnight cultures of BC, SPY and media control were centrifuged to remove bacterial cells. L-SRB was suspended in the supernatant ('S/N') and then retrieved by ultracentrifugation. The resultant liposome pellets were then washed once ('Wash') with PBS to remove non-specifically bound proteins and then centrifuged again. The final liposome pellets ('Pellet') were then analyzed by SDS-PAGE. Selected bands (numbered from 1 to 8) were then excised from the gel and sent for mass spectrometry analysis. FIG. 11B: Results of LC-ESI-MS analysis of the bands from (a) are shown here. The well-known membrane toxins, Alveolysin and Streptolysin O, were identified from BC and SPY respectively. The other 6 identified bands have been reported in literature as membrane-interacting proteins.

FIG. 12 shows that a quicker TTD can be achieved by decreasing the P-value threshold for positive beta-hemolysis. A table using SPY as an example is shown. All italicized values are TTDs in minutes.

FIG. 13 shows that varying potency against L-SRB exhibited by two classes of hemolytic proteins. Membrane-degrading enzymes such as phospholipases secreted by BC and CP show significantly higher L-SRB lysis at the end of a 15-hour incubation compared to SPY, SA and LM which secrete non-enzymatic pore forming toxins. Error bar summaries of the data are means±s.d. Experiments were repeated at least thrice. ***P<0.0001

DETAILED DESCRIPTION OF THE INVENTION

The present invention relates to the field of diagnostics and more particularly to the detection of beta-hemolytic pathogens. More specifically, the present invention relates to the rapid and accurate detection of beta-hemolytic pathogens using sterically-stabilized liposomes.

All known beta-hemolytic bacteria are pathogenic and hence the timely detection of beta-hemolysis is an invaluable positive predictor of pathogens. However, the evaluation of hemolysis on blood agar takes too long to impact clinical decision making. The present invention shows that beta-hemolytic bacteria are able to lyse and release fluorophores encapsulated in sterically-stabilized liposomes whereas alpha- and gamma-hemolytic bacteria have no effect and can thus be distinguished. By analyzing fluorescence kinetics, beta-hemolytic colonies cultured on agar are identifiable with 100% accuracy within 6 hours. In addition, static analysis based on fluorescence intensity and machine-extracted textural features distinguishes between beta-hemolytic and co-cultured control colonies with 99% accuracy. In broth cultures, beta-hemolytic bacteria were detectable in under an hour while control bacteria remained negative even the next day. The present invention shows that replacing red blood cells with sterically-stabilized liposomes can enable the rapid detection of beta-hemolysis.

The approach utilized in the present invention designed to obviate the problems in using red blood cell assays. A single bacterium, even if it manages to lyse a red blood cell 6 times its length and 130 times its volume, would not create a measurable event within a crowd of opaque blood cells. In contrast, the same bacterium would reasonably be expected to lyse multiple liposomes each a tenth of its length and a hundredth of its volume, giving rise to a visible fluorescent signal in transparent media (FIG. 1C). The present invention shows that liposomes sterically-stabilized with polyethylene glycol (PEG) can be lysed by beta-hemolytic bacteria but not alpha- or gamma-hemolytic bacteria. First, it is shown that only beta-hemolytic colonies cultured in agar can lyse liposomes encapsulating Hoechst 33342 (H33342), and as a result be stained by the released H33342. By classifying the colonies based on fluorescence intensity and fluorescence texture (using a novel pattern recognition approach), we were able to distinguish beta-hemolytic colonies are distinguished from alpha- and gamma-hemolytic colonies, regardless of whether they were pure cultures (100% accuracy) or admixtures of beta- and alpha-hemolytic bacteria (99% accuracy). The present invention further shows that liposomes encapsulating Sulforhodamine B (SRB) are able to detect beta-hemolysis in liquid media down to a single bacterium within hours. Finally, the present invention shows that the liposome bilayer, despite being PEGylated, is able to physically associate with proteins secreted by *Streptococcus pyogenes* and *Bacillus cereus* which are known to be membrane-active, an observation which is consistent with liposomes being a substrate for hemolysins [6].

Figure 1A:
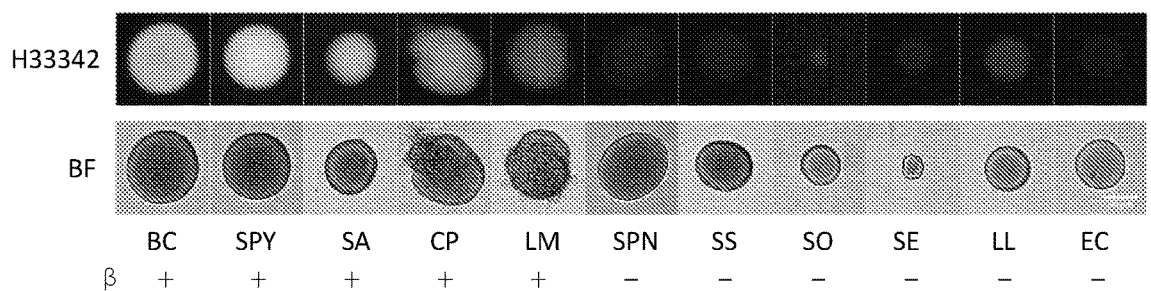
FIGS. 1A-1E show that beta-hemolytic colonies are differentially stained by L-Hoechst. Bacteria are labelled as follows. BC: *Bacillus cereus*, SPY: *Streptococcus pyogenes*, SA: *Staphylococcus aureus*, CP: *Clostridium perfringens*, LM: *Listeria monocytogenes*, SPN: *Streptococcus pneumoniae*, SS: *Streptococcus salivarius*, SO: *Streptococcus oxalis*, SE: *Staphylococcus epidermidis*, LL: *Lactococcus lactis*, EC: *Escherichia coli*. 'β+' and 'β−' refer to beta- and non-beta-hemolytic bacteria respectively.

The present invention provides a method for detecting the presence of beta-hemolytic pathogens in a sample. The method comprises: (a) adding a sample suspected of containing a beta-hemolytic pathogen to a growth medium containing sterically-stabilized liposomes comprising an encapsulated fluorophore to form a test assay mixture; (b) incubating the test assay mixture for a period of time sufficient for the beta-hemolytic pathogen, if present, to form a population of test cells and to cause lysis of the sterically-stabilized liposomes to release the fluorophore into the assay mixture for assimilation into the population of test cells; (c) detecting the fluorescence of the population of test cells; and (d) comparing the amount of fluorescence of the one or more test colonies with the amount of fluorescence of a population of control cells.

In some embodiments, the fluorophore is a DNA-binding dye that can associate with pathogens. In some embodiments, the fluorophore is assimilated by beta-hemolytic pathogens which then fluoresce. In some embodiments, the fluorophore is selected on the basis of the pathogens' permeability to the fluorophore. In one embodiment, the fluorophore is assimilated by gram-positive bacteria. In another embodiment, the fluorophore is assimilated by gram-negative bacteria. In some embodiments, a cell-wall permeabilizing agent may be used to enhance uptake by the pathogen. A suitable cell-wall permeabilizing agent is one which provides increased fluorescence but is not toxic to the pathogen at the concentration necessary to provide increase fluorescence. Examples of cell-wall permeabilizing agents are known in the art. In other embodiments, the fluorophore is selected on the basis of the background fluorescence of the growth medium. In some embodiments, the growth medium is a solid medium and the population of test cells form one or more test colonies. In some embodiments, the solid medium is agar-based. In other embodiments, the growth medium is a liquid medium. In some embodiments, the sterically-stabilized liposomes are liposomes stabilized by polyethylene glycol (PEG). In one embodiment, the PEG is PEG2000. In some embodiments, the sterically-stabilized liposomes are lysed by beta-hemolytic pathogens, but not by alpha- and gamma-hemolytic pathogens. In other embodiments, the pathogens are bacteria.

Other embodiments of the present invention are described in embodiments of the invention and description below and are included as embodiments of the invention. Other embodiments of the present invention are described in the Examples below and are included as embodiments of the invention.

In one embodiment, the present invention provides a method for detecting the presence of beta-hemolytic pathogens in a sample using a solid growth medium. In some embodiments, this method comprises: (a) adding a sample suspected of containing a beta-hemolytic pathogen to a solid growth medium containing sterically-stabilized liposomes comprising an encapsulated fluorophore to form an assay mixture; (b) incubating the assay mixture for a period of time sufficient for the beta-hemolytic pathogen, if present, to form one or more test colonies and to cause lysis of the sterically-stabilized liposomes to release the fluorophore into the assay mixture for assimilation into the one or more test colonies; (c) detecting the fluorescence of the one or more test colonies; and (d) comparing the amount of fluorescence of the one or more test colonies with the amount of fluorescence of one or more control colonies. In other embodiments, the method further comprises quantitating a textural component of the colony fluorescence of the one or more test colonies and the background fluorescence associated with the one or more control colonies.

In some embodiments, the fluorophore is a DNA-binding dye that can associate with pathogens. In some embodiments, the fluorophore is assimilated by beta-hemolytic pathogens which fluoresce as described herein. In some embodiments, the fluorophore is selected on the basis of the pathogens' permeability to the fluorophore. In one embodiment, the fluorophore is assimilated by gram-positive bacteria. In another embodiment, the fluorophore is assimilated by gram-negative bacteria. In other embodiments, the fluorophore is selected on the basis of the background fluorescence of the growth medium. In some embodiments, the solid growth medium is an agar-based solid medium. In other embodiments, the sterically-stabilized liposomes are liposomes stabilized by polyethylene glycol (PEG). In one embodiment, the PEG is PEG2000. In some embodiments, the sterically-stabilized liposomes are lysed by beta-hemolytic pathogens, but not by alpha- and gamma-hemolytic pathogens. In other embodiments, the pathogens are bacteria.

In some embodiments, the solid growth medium comprises Brain Heart Infusion (BHI). In other embodiments, the solid growth medium also comprises Fetal Bovine Serum (FBS). In some embodiments, the solid growth medium is agar-based and contains agarose. As described herein, the solid growth medium further contains the sterically-stabilized liposomes containing a fluorophore. In some embodiments, the solid growth medium comprises about 0.2× to about 1× BHI, 0% to about 10% FBS (v/v), about 0.5% to about 2% agarose (w/v), and about 1 μl to about 10 μl liposomes containing fluorophore. In other embodiments, the solid growth medium comprises about 1× BHI, about 10% FBS (v/v), about 1% agarose (w/v), and about 4 μl liposomes containing fluorophore. In some embodiments, the liposomes containing fluorophore are liposomes containing H33342 as described herein. In other embodiments, the solid medium components comprise 100 μl, although any amount may be used depending on the substrate, e.g., microscope slide, for performing the assay. In some embodiments, BHI is used because it is a complex rich media which supports the growth of a wide variety of bacteria. In other embodiments for the solid medium, BHI is substituted with other dehydrated liquid culture media including, but not limited to, Brucella Broth, Cooked Meat Medium, Reinforced Clostridial Medium, LB Broth, Nutrient Broth, Thioglycollate Medium, Todd Hewitt Broth, Terrific Broth and Tryptic Soy Broth. In other embodiments, BHI is substituted with ready-formulated dehydrated solid media including, but not limited to Brucella Agar, BHI Agar, LB Agar, Nutrient Agar and Tryptic Soy Agar. In some embodiments, a selective medium is used to enrich for target bacteria of choice in which case substitutes for BHI include, but are not limited to, Mannitol Salt Agar (preferably without phenol red) or Campylobacter Agar with antimicrobial selection. In other embodiments, the medium is directly supplemented with selective agents of choice including, but not limited to, antibiotics, salts, bile salts, dyes, tellurite and charcoal. In some embodiments, antibiotics include, but are not limited to, methicillin, vancomycin ampicillin, cefalothin, chloramphenicol, ciprofloxacin, erythromycin, kanamycin, rifampicin, tetracycline and trimethoprim.

In other embodiments, the fluorophore is a DNA-binding dye that can associate with pathogens. In some embodiments, the fluorophore is assimilated by beta-hemolytic pathogens which fluoresce. In some embodiments, the fluorophore is assimilated by gram-positive bacteria. In other embodiments, the fluorophore is assimilated by gram-negative bacteria. In some embodiments, a cell-wall permeabilizing agent may be used to enhance uptake by the pathogen. A suitable cell-wall permeabilizing agent is one which provides increased fluorescence but is not toxic to the pathogen at the concentration necessary to provide increase fluorescence. Examples of cell-wall permeabilizing agents are known in the art. In some embodiments, the fluorophore is Hoechst 33342 (H33342). In other embodiments DNA/RNA binding dyes in general can be used. In some embodiment, examples of such binding dyes include, but are not limited to: DAPI, Hoechst 33258, 34580, acridine orange, ethidium bromide, SYBR family of dyes, Picogreen, SYTO-60, STYO-62, SYTO-64, POPO-3, TOTO-3, BOBO-3, TO-PRO-3 and SYTOX Orange, as well as those described herein.

In some embodiments, the sterically-stabilized liposomes are formulated at the nanoscale using PEGylation or other conjugation for steric-stabilization [7] and saturated phosphatidylcholine coupled with high cholesterol content to decrease membrane permeability [8]. In other embodiments, the saturated phosphatidylcholine can be replaced by other membrane forming phospholipids. In some embodiments, the sterically-stabilized liposomes are prepared using conventional techniques or those described herein. In some embodiments the membrane forming phospholipids is a saturated phosphatidylcholine (PC), any synthetic phosphatidylcholine (PC) with saturated fatty acid tails, or membrane forming lipids. In some embodiments, synthetic PC may be dimyristoyl-phosphatidylcholine, dipalmitoyl-phosphatidylcholine, or distearoyl-phosphatidylcholine. In some embodiments, the saturated phosphatidylcholine (PC) is hydrogenated egg yolk phophatidylcholine (HEPC). In other embodiments, the membrane forming lipid may be saturated sphingomyelin, saturated phosphatidylethanolamine, saturated phosphatidylglycerol, saturated phosphatidylinositol or saturated phosphatidylserine. In some embodiments, the conjugate may be polyethylene glycol, polypropylene glycol, polybutylene glycol, or a copolymer of polyalkylene glycols such as a block copolymer of polyethylene glycol and polypropylene glycol), dextran, pullulan, ficoll, polyvinyl alcohol, styrene-maleic anhydride alternating copolymers, divinyl ether-maleic anhydride alternating copolymers, amylose, amylopectin, chitosan, mannan, cyclodextrin, pectin or carrageenan. In some embodiments, polyethylene glycol (PEG) is used as a conjugate (C-PEG). In some embodiments, the PEG has a molecular weight ranging from about 500 to about 10,000, preferably from about 1,000 to about 5,000, more preferably about 2,000. In some embodiments, PEG or other conjugate is conjugated with distearoyl phosphatidylethanolamine (DSPE), dipalmitoyl phosphatidylethanolamine (DPPE), dimyristoyl phosphatidylethanolamine (DMPE), distearoyl glycerol (DSG), dimyristoyl glycerol (DMG), cholesterylated-conjugate, Stearyl (STR) conjugate, C8 ceramide-conjugate or C16 ceramide-conjugate. In some embodiments, the conjugate is PEG2000 and the conjugate is DSPE-PEG2000, DPPE-PEG2000, DMPE-PEG2000, DSG-PEG2000, DMG-PEG2000, cholesterylated-PEG2000, STR-PEG2000, C8 ceramide-PEG2000 or C16 ceramide-PEG2000. In some embodiments, the sterically-stabilized liposomes are prepared from a preparative mixture of PC:cholesterol:C-PEG in which the molar ratio of PC:cholesterol is typically in the range of 2:1 to 1:1 with C-PEG typically present at 5% (mol/mol). In one embodiment, the preparative mixture of PC:cholesterol:C-PEG has a molar ratio of 50:45:5. In one embodiment, the preparative mixture is HEPC:cholesterol:DSPE-PEG2000.

In other embodiments, the sterically-stabilized liposomes with incorporated fluorophore are prepared by solubilizing the preparative mixture described herein in chloroform. This solution is dried to a thin film under rotary evaporation and then under vacuum overnight. The film is hydrated with a hydration buffer comprising 300 mM $(NH_4)_2SO_4$ and submerged in a waterbath sonicator at 70° C. for about 5 mins to 20 mins, preferably about 5 mins to about 15 mins, more preferably about 10 mins, to form multi-lamellar vesicles. These vesicles are further downsized by sonicating the solution with a probe sonicator to afford a clear solution (in some embodiments: 3-5 cycles of 2 minutes with 1 minutes rest in between). The mixture is kept on ice throughout sonication to prevent overheating of the suspension. To form an $H^+$ proton gradient for the loading of H33342, the liposome solution is dialyzed against 2 changes of saline solution (e.g., 0.15 M NaCl) at 2 and 4 hours and then left to dialyze overnight at 4° C. The fluorophore (e.g., H33342) is dissolved in saline and added to the liposome solution at a ratio of about 5:1 to about 20:1, preferably about 10:1 to about 15:1, more preferably about 10:1 (mol lipid:mol fluorophore (e.g., H33342)) and incubated in an oven at 70° C. for 2 hours. The liposome solution is passed through a HiTrap desalting column with PBS to remove unencapsulated (unincorporated) fluorophore (e.g., H33342). Fractions with a signal/background ratio of >100 are pooled together and stored at 4° C.

In some embodiments, a sample suspected of containing a beta-hemolytic pathogen is added to the solid growth medium described herein to form an assay mixture. In some embodiments the sample is a human or veterinary clinical samples (e.g., throat swabs, urine, stool, serum, plasma), food samples (e.g., from food processing facilities), or environmental samples (e.g., soil). In other embodiments, the assay mixture is vortexed and spun briefly to reconsolidate the mixture. In some embodiments, the assay mixture is placed on a concave microscope slide and a cover slip placed over it. In other embodiments, different forms of microscope slides may be used as long as they can accommodate the growth substrate and reagents. For example, microscope slides with reaction wells. Besides the slide format, petri dishes, multiwell plates (or other transparent culture receptacle) may also be used. In some embodiments, the assay mixture is incubated for a sufficient length of time for the beta-hemolytic bacteria, if present, to form test colonies. In other embodiments, the assay mixture is incubated for about 2 to about 24 hours, or overnight, in a humidified chamber at a temperature between about 10° C. to about 50° C. to form test cells. In some embodiments, the temperature for incubation is 37° C. In some embodiments, the assay mixture is incubated for about 5 to about 18 hours. In other embodiments, the assay mixture is incubated for about 6 to about 15 hours. In some embodiments, the assay mixture is incubated for about 6 to about 10 hours.

In some embodiments, the fluorescence is then detected, for example, by visualization and quantification using conventional techniques. In some embodiments, illumination for fluorescence excitation may be achieved in multiple ways including a lamp, laser or LED source. In some embodiments the fluorophore is H33342, and the test colonies are excited at 365 nm and the emission at 395 nm is captured. In some embodiments, the emission is captured with a suitable camera, such as a CCD camera. In some embodiments, the images are stored on a computer medium or in cloud storage. In some embodiments, analysis of the images is performed locally, e.g., on site. In other embodiments, analysis of the images is performed remotely, e.g., not at the site where the assay is performed. In some embodiments, the remote analysis could be performed in a different country from where the assay was performed. In some embodiments, quantitative analysis of fluorescence images in is performed using FIJI [22]. In some embodiments, the images are firstly stacked together and a fixed area was defined in the colony to measure the mean of the intensity. In some embodiments, background readings are obtained by using the same defined dimensions to measure the fluorescence intensity outside the colony. In some embodiments, the signal/background ratio is calculated by taking the mean intensity of the area in the colony divided by the mean intensity of the background. In some embodiments, control colonies are similarly incubated and detected by visualization and quantification. In some embodiments, the quantified fluorescence of the test colonies and control colonies are compared to detect presence of beta-hemolytic pathogens, e.g., bacteria. In other embodiments, the significant increase in fluorescence in the one or more test colonies compared to the one or more control colonies confirms the presence of beta-hemolytic pathogens, e.g., bacteria, in the sample.

In some embodiments, the method further comprises quantitating a textural component of the colony fluorescence of the one or more test colonies and the background fluorescence associated with the one or more control colonies. These embodiments are based on the observation that the colony fluorescence associated with beta-hemolysis was qualitatively different from background fluorescence associated with control bacteria. Specifically, the first looked uniform whereas the second had a granular texture. In some embodiments, the textural component is quantitated by computing a Dissimilarity parameter using the Grey Level Co-occurrence Matrix (GLCM) of the fluorescent colonies. GLCM is well known in the art and is illustrated in the Examples. Beta-hemolysis was found to be inversely proportional to Dissimilarity, hence creating a second complementary axis to separate beta-hemolysis from controls.

Other embodiments of the present invention are described in the description below and are included as embodiments of the invention. Other embodiments of the present invention are described in the Examples below and are included as embodiments of the invention.

In another embodiment, the present invention provides a method for detecting the presence of beta-hemolytic pathogens in a sample using liquid growth medium. In some embodiments, this method comprises: (a) adding a sample suspected of containing a beta-hemolytic pathogen to a liquid growth medium containing sterically-stabilized liposomes comprising an encapsulated fluorophore to form an assay mixture; (b) incubating the assay mixture for a period of time sufficient for the beta-hemolytic pathogen, if present, to form a population of test cells and to cause lysis of the sterically-stabilized liposomes to release the fluorophore into the assay mixture for assimilation into the population of test cells; (c) detecting the fluorescence of the population of test cells; and (d) comparing the amount of fluorescence of the population of test cells with the amount of fluorescence of a population of control cells. In other embodiments, the method further comprises determining the Time-To-Detection (TTD). TTD is defined as the point when fluorescence of a time-series significantly exceeds that of S. pneumoniae at $p<0.005$.

In some embodiments, the fluorophore is a DNA-binding dye that can associate with pathogens. In some embodiments, the fluorophore is assimilated by beta-hemolytic pathogens which fluoresce as described herein. In other embodiments, the sterically-stabilized liposomes are liposomes stabilized by polyethylene glycol (PEG). In one embodiment, the PEG is PEG2000. In some embodiments, the sterically-stabilized liposomes are lysed by beta-hemolytic pathogens, but not by alpha- and gamma-hemolytic pathogens. In other embodiments, the pathogens are bacteria.

In some embodiments, the liquid growth medium comprises Brain Heart Infusion (BHI). In other embodiments, the liquid growth medium comprises Fetal Bovine Serum (FBS). In some embodiments, the solid growth medium comprises about 0.2× to about 1× BHI, 0% to about 10% FBS (v/v), and about 1 μl to about 10 μl liposomes containing fluorophore. In other embodiments, the solid growth medium comprises about 1× BHI, about 10% FBS (v/v), and about 4 μl liposomes containing fluorophore. In some embodiments, the liposomes containing fluorophore are liposomes containing SRB as described herein. In other embodiments, the liquid medium components comprise 50 μl, although any amount may be used depending on the substrate, e.g., microwells, for performing the assay. In some embodiments, the liquid growth medium further comprises an antioxidant to create an anoxic environment for detecting anaerobic beta-hemolytic pathogens. In some embodiments, BHI is used because it is a complex rich media which supports the growth of a wide variety of bacteria. In other embodiments for the liquid medium, BHI is substituted with other dehydrated liquid culture media including, but not limited to, Brucella Broth, Cooked Meat Medium, Reinforced Clostridial Medium, LB Broth, Nutrient Broth, Thioglycollate Medium, Todd Hewitt Broth, Terrific Broth and Tryptic Soy Broth. In some embodiments, a selective medium is used to enrich for target bacteria of choice. in which case substitutes for BHI include, but are not limited to, Mannitol Salt Agar (preferably In some embodiments, the medium is directly supplemented with selective agents of choice including, but not limited to, antibiotics, salts, bile salts, dyes, tellurite and charcoal. In some embodiments, antibiotics include, but are not limited to, methicillin, vancomycin ampicillin, cefalothin, chloramphenicol, ciprofloxacin, erythromycin, kanamycin, rifampicin, tetracycline and trimethoprim. In some embodiments, the liquid growth medium further comprises an antioxidant to create an anoxic environment for detecting anaerobic beta-hemolytic pathogens. In some embodiments, the antioxidant is an enzyme system that removes dissolved oxygen from a liquid. In some embodiments, the enzyme system is Oxyrase® antioxidant enzyme system.

In other embodiments, the fluorophore is a DNA-binding dye that can associate with pathogens. In some embodiments, the fluorophore is assimilated by beta-hemolytic pathogens which fluoresce. In some embodiments, the fluorophore is assimilated by gram-positive bacteria. In other embodiments, the fluorophore is assimilated by gram-negative bacteria. In some embodiments, a cell-wall permeabilizing agent may be used to enhance uptake by the pathogen. A suitable cell-wall permeabilizing agent is one which provides increased fluorescence but is not toxic to the pathogen at the concentration necessary to provide increase fluorescence. Examples of cell-wall permeabilizing agents are known in the art. In some embodiments, the fluorophore is a non-membrane permeable fluorescent dye which is able to exhibit self-quenching. Such dyes include, but are not limited to, fluorescein, fluorescein analogues such as 5,6-carboxyfluorescein, rhodamine, rhodamine analogues, DAPI, Hoechst 33258, Hoechst 34580, acridine orange, SYBR dyes, SYTO-60, STYO-62, SYTO-64, POPO-3, TOTO-3, BOBO-3, TO-PRO-3 and SYTOX Orange. In some embodiments, the dye is Sulforodamine (SR). In one embodiment, the Sulforhodamine is Sulforhodamine B (SRB)

In some embodiments, the sterically-stabilized liposomes are formulated as described herein. In some embodiments, the sterically-stabilized liposomes with incorporated fluorophore are prepared by solubilizing the preparative mixture described herein in chloroform. This solution is dried to a thin film under rotary evaporation and then under vacuum overnight. The film is hydrated with a hydration buffer comprising fluorophore (e.g., SRB) and Phosphate Buffered Saline (PBS). In some embodiments, the amount of dye is selected to provide a suitable higher signal to background. In some embodiments, quenching starts to be effective above 50 mM of SRB. However, higher concentrations lead to greater quenching and dequenching and hence a higher signal to background. In some embodiments the hydration buffer comprises 100 mM SRB in PBS, pH 8.0-8.5. The hydrated film is submerged in a waterbath sonicator at 70° C. for about 5 mins to 20 mins, preferably about 5 mins to about 15 mins, more preferably about 10 mins, to form multi-lamellar vesicles. These vesicles are further downsized by sonicating the solution with a probe sonicator to afford a clear solution (in some embodiments: 3-5 cycles of 2 minutes with 1 minutes rest in between). The mixture is kept on ice throughout sonication to prevent overheating of the suspension. Finally, the liposome suspension is passed through a HiTrap desalting column with PBS to remove unencapsulated (unincorporated) fluorophore (e.g., SRB). Fractions with a signal/background ratio of >50 are pooled together and stored at 4° C.

In some embodiments, a sample suspected of containing a beta-hemolytic pathogen is added to the liquid growth medium described herein to form an assay mixture. In some embodiments the sample is a human or veterinary clinical samples (e.g., throat swabs, urine, stool, serum, plasma), food samples (e.g., from food processing facilities), environmental samples (e.g. soil). In other embodiments, the assay mixture is vortexed and spun briefly to reconsolidate the mixture. In some embodiments, the assay mixture is placed in wells of a well plate. In some embodiments, the well plate is a 384 well plate. In other embodiments, any transparent fluid receptacle which is compatible with fluorescence may be used. Example include, but are not limited to, multiwell plates of any format, test tubes, cuvettes and slides with wells to hold the test reagents. Besides a fluorescence multiwell plate reader, any instrument which is capable of analyzing a fluorescence signal may be used. For example, an LED excitation source illuminating the sample in combination with an appropriate filter over a CCD camera would work. In some embodiments, the assay mixture is incubated for a sufficient length of time for the beta-hemolytic bacteria, if present, to form a population of test cells. In other embodiments, the assay mixture is incubated for about 5 minutes to about 30 minutes or for about 20 minutes to about 15 hours, in a chamber which may or may not be humidified at about 10° C. to about 50° C. to form test cells. In some embodiments, the incubation is performed at 37° C. to form test cells.

In some embodiments, the fluorescence is then detected, for example, by visualization and quantification using conventional techniques. In some embodiments, a fluorescence multiwell plate reader or any instrument which is capable of analyzing a fluorescence signal may be used. For example, an LED excitation source illuminating the sample in combination with an appropriate filter over a CCD camera can be used for capturing images of the fluorescence. In some embodiments the fluorophore is Hoechst 33342, and the cells are excited at 365 nm and the emission at 395 nm is captured. In some embodiments, the emission is captured with a suitable camera, such as a CCD camera. In some embodiments, a population of cells from wells of the well plate are collected, washed, normalized to a fixed number and heat fixed to a microscope slide. In some embodiments the fluorophore is SRB, and the cells are excited at 526 nm and the emission at 584 nm with a gain of 70 is captured. In some embodiments, the emission is captured with a suitable camera, such as a CCD camera. In some embodiments, the images are stored on a computer medium or in cloud storage. In some embodiments, analysis of the images is performed locally, e.g., on site. In other embodiments, analysis of the images is performed remotely, e.g., not at the site where the assay is performed. In some embodiments, the remote analysis could be performed in a different country from where the assay was performed. In some embodiments, quantitative analysis of fluorescence images is performed using FIJI [22] as described herein. In some embodiments, a population of control cells are similarly incubated and detected by visualization and quantification. In some embodiments, the quantified fluorescence of the population of test cells and population of control cells are compared to detect presence of beta-hemolytic pathogens, e.g., bacteria.

In other embodiments, the fluorescence in test wells of the well plate is detected and compared to the fluorescence of control wells in the well plate. In some embodiments, the control wells contain a control population of an alpha- or gamma-hemolytic pathogen, such as an alpha- or gamma-hemolytic bacteria. An alpha- or gamma-hemolytic bacteria is chosen because it only lysed up to 0.5% of the liposomes when normalized to the fluorescence signal of 100% liposome lysis. In some embodiments, the control pathogen is *S. pneumoniae* or Viridans Streptococci (e.g., *Streptococcus salivarius, Streptococcus mitis* or *Streptococcus mutans*). In some embodiments, the population of beta-hemolytic cells in the test wells lysed about 10% to about 65% of the liposomes which results in signal levels 26-125 times above the control population of cells. In some embodiments the fluorophore is SRB, and the fluorescence of the cells in the wells is detected with excitation at 526 nm and the emission is measured at 584 nm with a gain of 70. In other embodiments, the significant increase in fluorescence in the test wells compared to the control wells confirms the presence of beta-hemolytic pathogens, e.g., bacteria, in the sample.

In other embodiments, the method further comprises determining the Time-To-Detection (TTD). TTD is defined as the point when fluorescence of a time-series significantly exceeds that of *S. pneumoniae* at $p<0.005$. In some embodiments, the fluorescence of the test and control wells is determined as described herein every ten minutes for up to 15 hours of incubation of the well plate until the fluorescence in the test wells significantly exceeded that of *S. pneumoniae*. This assay is sensitive at the single cell level with the limit of detection ranging from 1-10 CFUs. The quickest detection time for $10^4$ CFUs of *S. pyogenes* is 50 minutes and the slowest detection time for a single CFU of *S. aureus* is 14.3 hours which was still within a day for a statistical stringency of P<0.001. In some embodiments, decreasing statistical stringency from P<0.001 to P<0.05 allows for faster detection. For example, $10^4$ CFUs of *S. pyogenes* can be detected within 18 minutes using this threshold.

Other embodiments of the present invention are described in the description below and are included as embodiments of the invention. Other embodiments of the present invention are described in the Examples below and are included as embodiments of the invention.

The present invention also provides a kit for conducting methods or assays described herein for detecting beta-hemolytic pathogens. In some embodiments, the pathogen is a bacteria. In some embodiments, the kit comprises sterically-stabilized liposomes as described and a fluorophore. The sterically-stabilized liposomes are lysed by a beta-hemolytic pathogen and are not lysed by an alpha-hemolytic pathogen or by a gamma-hemolytic pathogen. In some embodiments the fluorophore is encapsulated in the liposomes as described herein. In other embodiments, the fluorophore is separate from the liposomes and encapsulated into the liposomes prior to use as described herein. In some embodiments, the kit further comprises a growth medium. In some embodiments, the growth medium is a solid growth medium as described herein. In other embodiments, the growth medium is a liquid growth medium as described herein. In some embodiments, the kit also comprises a control pathogen as described herein. In some embodiments, the kit further comprises instructions for carrying out the method or assay. In some embodiments, the kit components are packaged in one or more suitable containers.

The present invention also provides for use of sterically-stabilized liposomes comprising an encapsulated fluorophore described herein for the detection of beta-hemolytic pathogens. In some embodiments, the pathogen is a bacteria. The present invention further provides for the use of a kit described herein for the detection of beta-hemolytic pathogens. In some embodiments, the pathogen is a bacteria.

Red blood agar plates are both robust in sensitivity down to a single cell, and specific with low false positives. They do however have several drawbacks. Firstly, they require long incubation times. In the clinical context, the information from red blood agar plates is not timely enough to influence clinical decisions. Secondly, the large format of the petri dish limits the extent to which such testing may be scaled and is a waste of resources in terms of the materials that go into the plate. Thirdly, the requirement for blood products from horses and sheep are a potential risk of zoonotic disease transmission, an especially relevant consideration in the context of clinical or food safety testing. The present invention shows that one way to solve these problems is by directly replacing erythrocytes with liposomal dyes.

The idea of perturbing lipid vesicles with hemolysins is not novel in itself [16-18]. For example, Thet et al created an liposome based assay to distinguish *S. aureus* from *Pseudomonas aeruginosa* by altering the concentrations of cholesterol and the polymerizable amphiphile 10,12-tricosadiynoic acid. However, what has not been described before is the overarching principle that liposomes sterically stabilized with PEG are sufficiently stable to distinguish beta-hemolysis from alpha- and gamma-hemolysis. It is demonstrated herein that such liposomes can indeed be biosensors to distinguish beta-hemolytic bacteria from alpha- and gamma-hemolytic bacteria with high accuracy. The ability of liposomes to distinguish beta-hemolytic bacteria from alpha- and gamma-hemolytic bacteria was proved in two parts, the direct microscopic visualization of beta-hemolytic colonies on agar and the rapid and indirect detection of beta-hemolysins in broth. The PEG sterically stabilized liposomes were verified to be stable when suspended in rich growth liquid media and agar (FIG. 2; FIG. 4B). Visualization of colonies in agar presented an additional challenge which required the released dye to be assimilated by beta-hemolytic bacterial colonies instead of freely diffusing away.

Figure 1B:
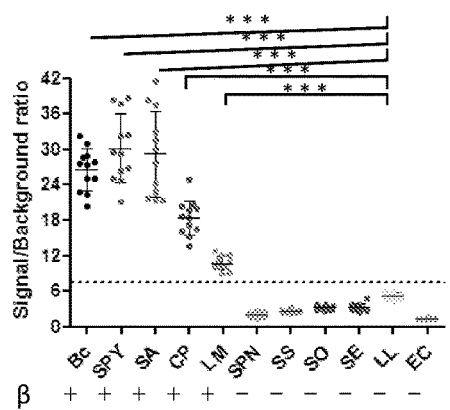
Figure 1C:
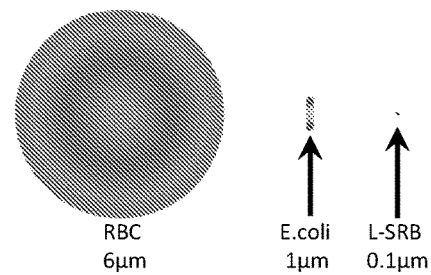

In the first part, it was shown that beta-hemolytic colonies lyse L-Hoechst on agar after overnight incubation, becoming fluorescent in the process. Non-hemolytic colonies had low baseline fluorescence from uptake of trace H33342. Although H33342 is not taken up by gram-negative bacteria, the principles described are equally applicable to gram-negative bacteria if a suitable dye that is assimilated by gram-negative bacteria is used. If required, individual colonies can be isolated from the agar for further downstream characterization. The use of the Dissimilarity parameter from GLCM creates a second dimension which complements integrated colony fluorescence intensity in assessing beta-hemolysis. When plotted along both axes, all beta-hemolytic colonies are linearly separable from controls. This included *L. monocytogenes* which is typically known to be notoriously time-consuming, requiring 24-48 hours of enrichment on selective media with a total test time of 5-7 days [19]. When cultured on sheep blood agar, hemolysis is often observed not to extend beyond the edge of colonies, sometimes necessitating the removal of the colonies to observe the zone of clearing. In comparison, the present invention identified *L. monocytogenes* beta-hemolysis using a generic growth media and with just an overnight incubation (FIGS. 1A and 1B). This technique also worked well with bacterial admixtures. In clinical settings, human pathogens such as *S. pyogenes* and *S. aureus* are often commingled with the commensal *S. pneumoniae*. By labelling *S. pneumoniae* with Alexa-Fluor 488 antibodies the present invention showed that both *S. pyogenes* and *S. aureus* could clearly be differentiated from *S. pneumoniae* (FIGS. 4A-4D).

Figure 5A:
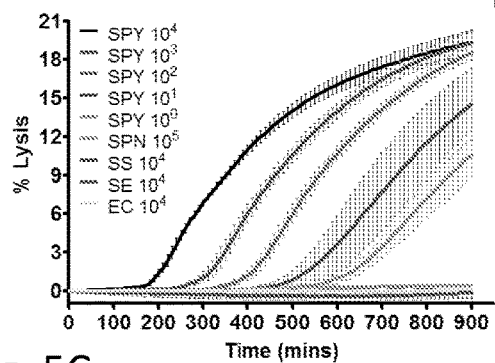
FIGS. 5A-5H show that beta-hemolytic bacteria are rapidly detectable in broth media with L-SRB.
Figure 5B:
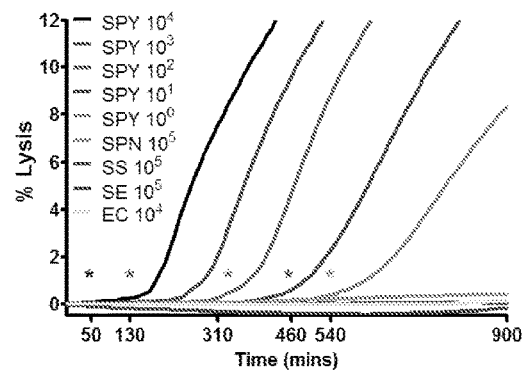
Figure 5C:
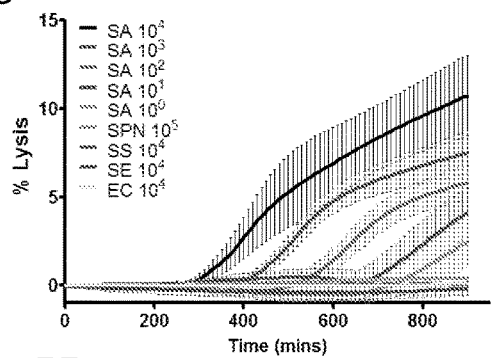
Figure 5D:
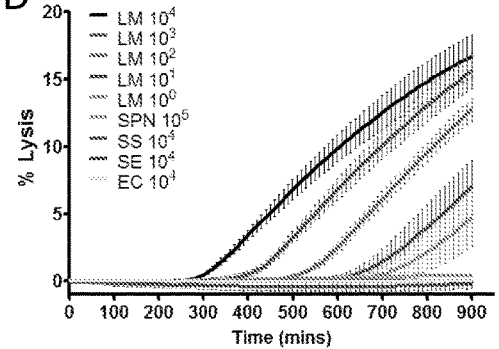
Figure 5E:
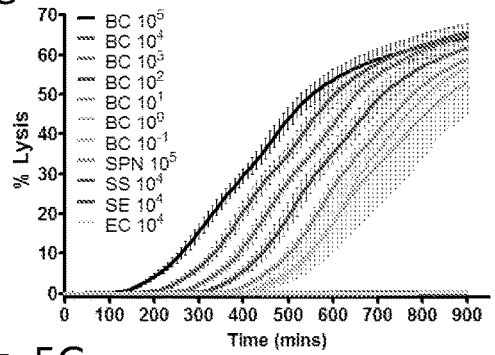
Figure 5F:
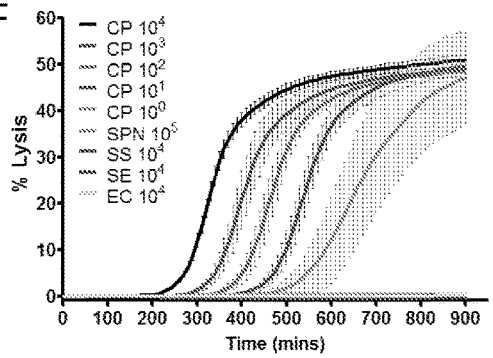
Figure 5G:
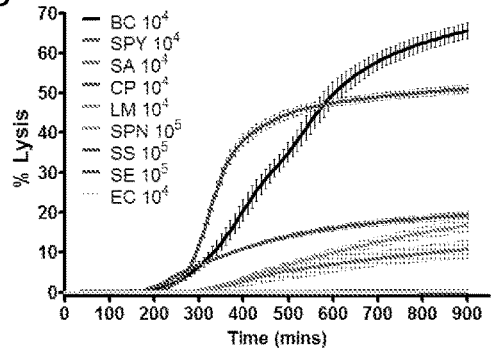
Figure 5H:
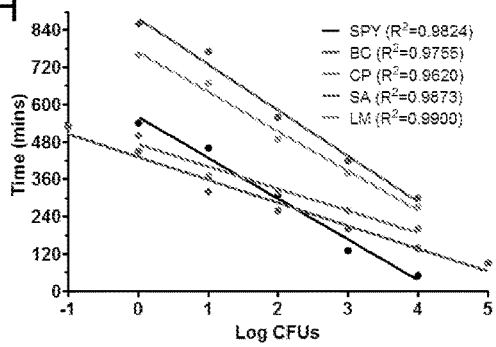
Figure 5I:
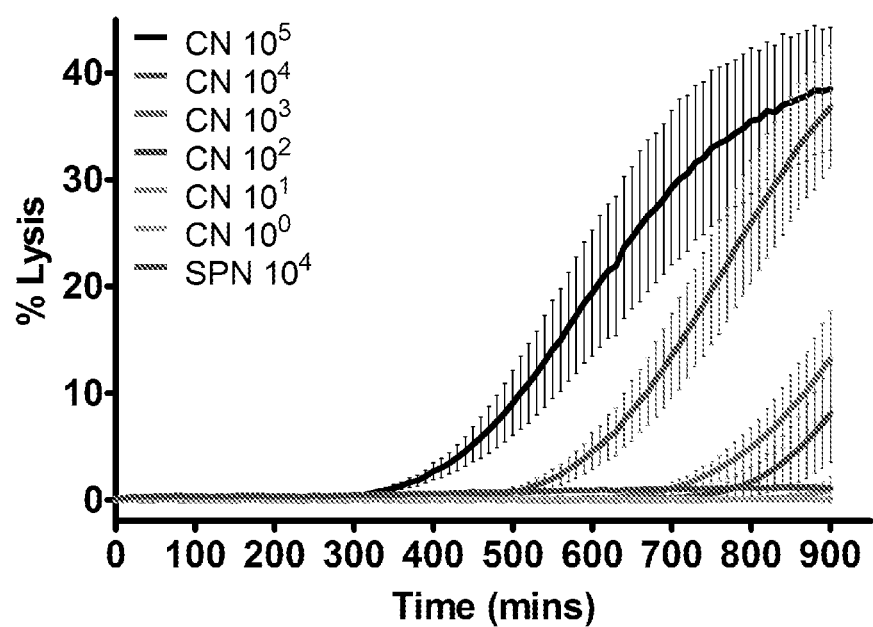
FIG. 5I shows that the beta-hemolytic bacterium *Clostridium novyi*-NT (CN), a strict anaerobe which is extremely difficult to isolate and culture and which is a close relative of the foodborne pathogen *Clostridium botulinum*, is rapidly detectable in broth media with L-SRB. CN was inoculated in 384-well plates containing BHI broth, Fetal Bovine Serum, Oxyrase™ and L-SRB. All exponents stated in the legends refer to the inoculum size in CFUs. CN was observed to lyse L-SRB and cause a sharp increase in SRB fluorescence reported as % Lysis. In contrast, alpha-hemolytic (SPN) bacteria did not show an appreciable increase in signal. Each time series was derived from at least three replicates. Error bars, means±s.d.
Figure 6A:
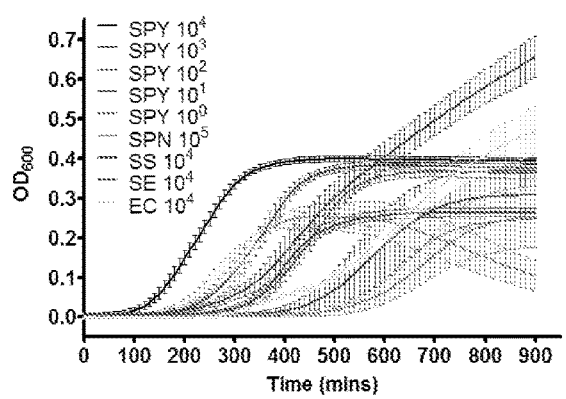
FIGS. 6A-6D show growth curves of SPY, SA, CP and LM over the course of the experiment.
Figure 6B:
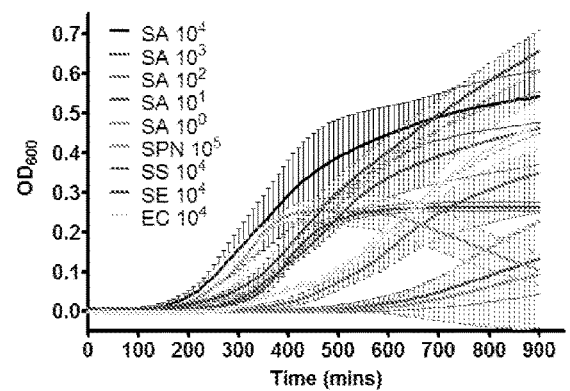
Figure 6C:
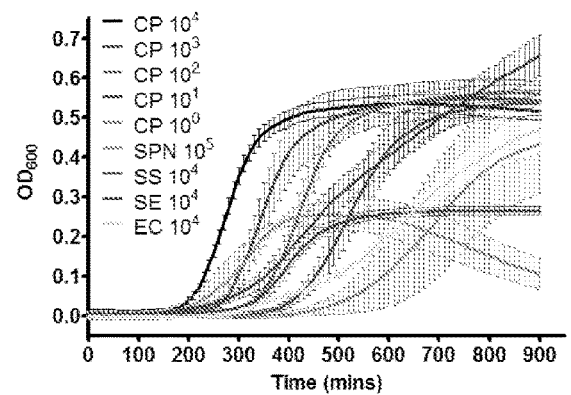
Figure 6D:
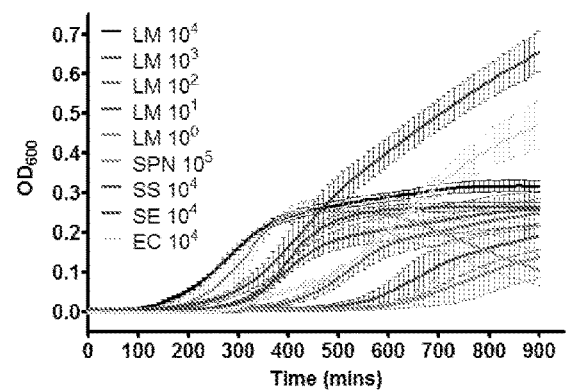
Figure 7A:
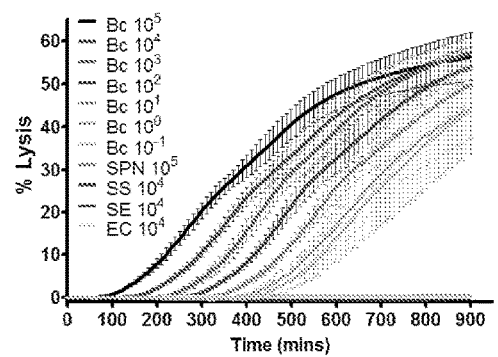
FIGS. 7A-7D). Each time series was shown from three independent experiments, each with four replicates.
Figure 7B:
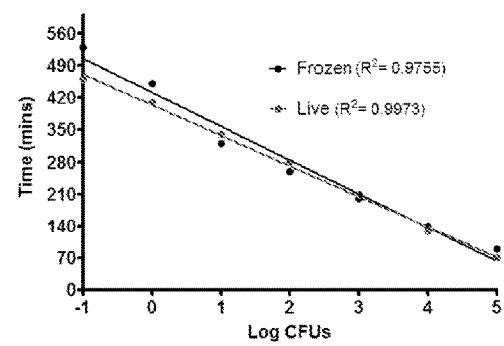
Figure 7C:
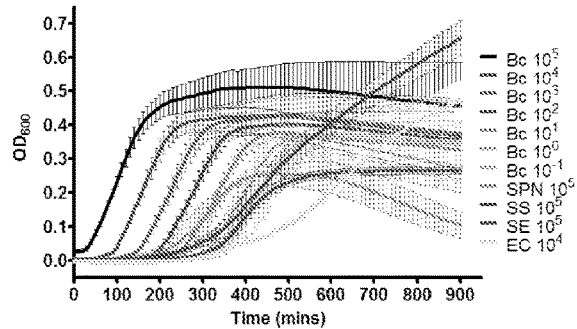
Figure 7D:
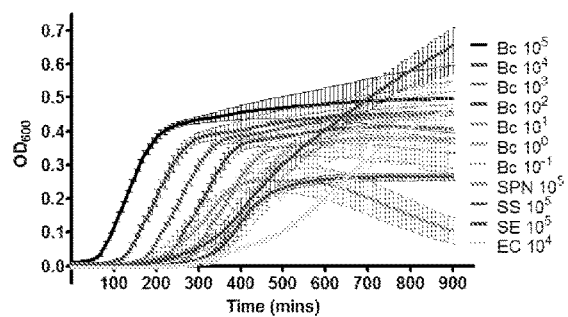

In the second part, beta-hemolysis was detected in broth using a 384-well plate format. Here, beta-hemolytic bacteria were observed to generate a fluorescent signal at least 26 fold above baseline (FIG. 5G). *S. pneumoniae* was chosen as the baseline because it is strongly alpha-hemolytic and a common commensal. Using its fluorescence time-series as the null hypothesis, the time point of the five betat-hemolytic bacteria tested when their fluorescence exceeded *S. pneumoniae*'s in a statistically significant manner was measured. These time points termed time-to-detection (TTD) correlated linearly with inoculum size (FIG. 5H). The assay was sensitive at the single cell level with the limit of detection for all 5 bacteria ranging from 1-10 CFUs. The quickest detection time for $10^4$ CFUs of *S. pyogenes* was in 50 minutes and the slowest detection time for a single CFU of *S. aureus* was in 14.3 hours which was still within a day. Decreasing statistical stringency from P<0.001 to P<0.05 allows for faster detection. For example, $10^4$ CFUs of *S. pyogenes* can be detected within 18 minutes using this threshold (FIG. 12). The infectious doses for *B. cereus, S. pyogenes, C. perfringens, S. aureus* and *L. monocytogenes* are $10^5$, $10^3$, $10^7$, $10^5$ and $10^3$ respectively [19-21], which was well within the span of inoculums used in the experiments. Admixture experiments with *B. cereus* and *S. pneumoniae* proved that even single CFUs of *B. cereus* (far below its infectious dose) are still detectable despite the presence of an overwhelming excess of *S. pneumoniae*.

Figure 13:
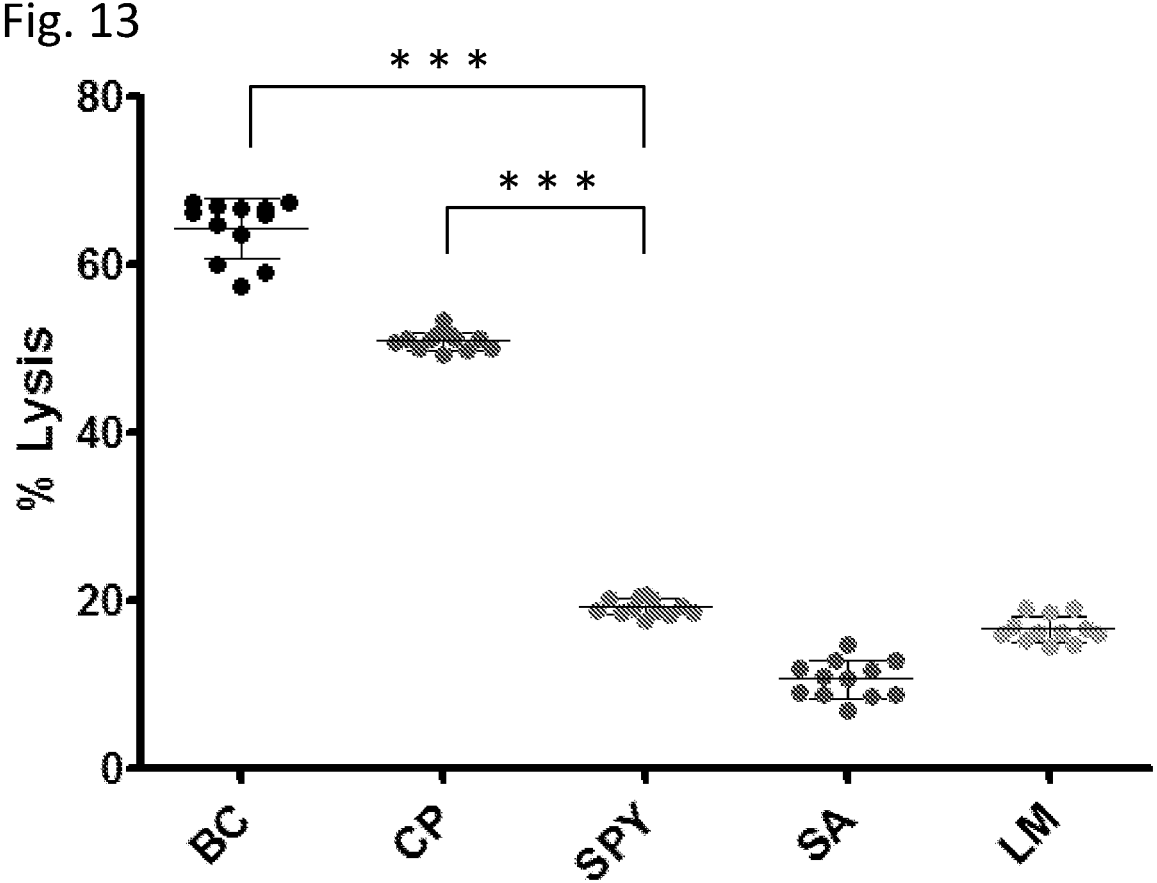

One observation that was found interesting was that *B. cereus* and *C. perfringens*, both of which secrete phospholipases, had a much higher signal after an overnight incubation as compared to *S. pyogenes, S. pyogenes, L. monocytogenes* and *S. aureus*, all of which secrete pore-forming hemolysins (FIG. 13). Despite this difference, the TTDs for all bacteria did not differ by more than a magnitude and the fastest TTD was $10^4$ CFUs of *S. pyogenes*, demonstrating that hemolysin class is not the determining factor for TTD. It is speculated that the decreased asymptotic signal for pore-forming toxins as compared to phospholipases is due to differences in how these proteins interact with membranes. Pore-forming proteins, once assembled within the bilayer do not transition easily into the bilayers of other intact liposomes. A phospholipase on the other hand has continued activity over its lifetime.

In the final experiment, liposomes incubated with media conditioned with the growth of *B. cereus* or *S. pyogenes* was isolated to see if membrane interacting hemolysins could be isolated. From *S. pyogenes*-conditioned media, Streptolysin O, the main aemolysin in this bacterium, was isolated. Interestingly when this experiment was repeated with *B. cereus*, three well-defined membrane interacting proteins, Alveolysin, Enterotoxin and Enterotoxin B, were isolated, but the main hemolysin which was Phospholipase C (FIGS. 11A and 11B) was not isolated. This is consistent with the earlier speculation that pore forming proteins have a higher affinity for bilayers compared to phospholipases. The fact that the liposomes were PEGylated did not compromise protein binding, demonstrating the utility of PEGylated liposomes for investigating protein-bilayer interactions.

Aspects of the instant beta-hemolytic pathogen assay can be customized to create specialized applications. For example, the liposomal composition may be altered to assay for substrate-specific hemolysins such as sphingomyelinase. The high stability of the liposomal components implies a long shelf-life and compatible with other assay components in a one-pot or master mix formats. Further, the assay is easily adaptable to a high throughput through automation using multiple fluorescent dyes of choice, various sources of fluorescent excitation (such as LEDs), cameras, motorized stages and image analysis software for fully automated monitoring. If urgency is paramount, the time to detection can be further minimized by using real time image processing and pattern recognition algorithms to detect the first moments of incipient beta-hemolysis.

In summary, the present invention demonstrates a novel means of detecting hemolysis based on liposomal technology with the potential for shortening diagnoses of a multitude of beta-hemolytic pathogens to less than a day, thus enabling quicker and more confident decision making for food safety applications and detection of potentially life-threatening pathogens.

EXAMPLES

The present invention is described by reference to the following Examples, which are offered by way of illustration and are not intended to limit the invention in any manner. These Examples represent further embodiments of the invention described above in the detailed description. Standard techniques well known in the art or the techniques specifically described below were utilized.

Example 1

Materials and Methods

Materials and bacterial strains: Hydrogenated egg phosphatidylcholine (527600), 1,2-distearoyl-sn-glycero-3-phosphoethanolamine-N-[amino(polyethylene glycol)-2000], sodium salt (DSPE-PEG2000, 588200) were purchased from Lipoid AG, Switzerland. Fetal bovine serum (F7524), 4-(2-hydroxyethyl)-1-piperazineethanesulfonic acid (HEPES, 83264), cholesterol (C8667) and BHI (Brain Heart Infusion, 53283, Fluka) were purchased from Sigma-Aldrich. Hoechst 33342 (H33342, H1399) was purchased from Life Technologies.

The bacteria strains used in this study were *Bacillus cereus* (ATCC 10987), *Clostridium perfringens* (ATCC 13124), *Clostridium novyi*-NT (a kind gift from the Ludwig Center at Johns Hopkins), *Listeria monocytogenes* (MBL.0129E3-CRM, Microbiologics ATCC 13932), *Streptococcus salivarius* (ATCC 13419), *Streptococcus oxalis* (ATCC 9811) and *Lactococcus lactis* subsp. *lactis* (ATCC 11454). *Streptococcus pyogenes* and *Streptococcus pnuemoniae* (generously provided by National University Hospital), *Staphylococcus epidermis* and *Staphylococcus aureus* (a kind gift from Department of Biological Sciences, National University of Singapore), laboratory *E. coli* strains XL1-blue and DH5α. (Refer to Table 1). All work with these bacteria was reviewed and approved by the Temasek Life Sciences Laboratory Institutional Biosafety Committee (Reference # IBC-050413-15-IC).

TABLE 1

Bacterial Strains

| Bacteria | Hemolytic response on blood agar | Source |
| --- | --- | --- |
| *Bacillus cereus* | Beta hemolysis | ATCC 10987 |
| *Streptococcus pyogenes* | Beta hemolysis | NUH |
| *Staphylococcus aureus* | Beta hemolysis | NUS |
| *Clostridium perfringens* | Beta hemolysis | ATCC 13124 |
| *Clostridium* novp-NT | Beta hemolysis | Gift from the Ludwig Center at Johns Hopkins |
| *Listeria monocytogenes* | Beta hemolysis after prolonged incubation over days | Microbiologics ATCC 13932 |
| *Streptococcus pnemoniae* | Alpha hemolysis | NUH |
| *Streptococcus salivarius* | Alpha hemolysis | ATCC 13419 |
| *Staphylococcus epidermidis* | Gamma hemolysis | NUS |
| *Streptococcus oralis* | Gamma hemolysis | ATCC 9811 |
| *Lactococcus lactis* subsp. *lactis* | Gamma hemolysis | ATCC 11454 |
| *E colt* XL1-blue, DH5α | Gamma hemolysis | Temasek Lifesciences Laboratory |

Bacterial strains obtained from the above sources were streaked on a sheep blood agar to check for hemolytic activity. Single colonies were then inoculated into 3 ml of sterile BHI (237500, BD Bacto) and incubated at 37° C. without shaking overnight. The overnight cultures were then further diluted 1:100 into 5 ml of fresh BHI media and allowed to grow till an $OD_{600}$ of 0.35-0.6. These early exponential phase cultures were diluted 1:1 in 30% glycerol and stored at −80° C. in aliquots. *L. monocytogenes*, and the laboratory *E. coli* strain, XL1-blue and DH5α were grown up the same way, except with shaking at 180 rpm. These frozen stocks were used in subsequent experiments.

Passive encapsulation of SRB into liposomes: A mixture of HEPC:Cholesterol:DSPE-PEG2000 at a molar ratio of 50:45:5 was solubilized in chloroform. This solution was dried to a thin film under rotary evaporation and then under vacuum overnight. Hydration buffers were prepared fresh prior to use. Sulforhodamine B (SRB, S1402, Sigma-Aldrich) hydration buffer was prepared as follows: SRB was dissolved in PBS with NaOH added to aid dissolution to give a final solution of 100 mM SRB, PBS pH 8.0-8.5

The film was hydrated with the hydration buffer and submerged in an Elma S30H water bath sonicator at 70° C. for 10 mins to form multi-lamellar vesicles. These vesicles were further downsized by sonicating the solution with a Qsonica Misonix probe sonicator to afford a clear solution (3-5 cycles of 2 minutes with 1 minutes rest in between). The mixture was kept on ice throughout sonication to prevent overheating of the suspension. Finally, the liposome suspension was passed through a HiTrap desalting column (G13/17-1408-01, GE Healthcare) with PBS to remove unencapsulated dye. Fractions with a signal/background ratio of >50 were pooled together and stored at 4° C.

Remote loading of H33342 dye into liposomes: Remote loading of molecules into liposomes was done according to the method described by Haran et al. [10]. Briefly, the liposomal suspension was prepared as described above with the exception of a 300 mM $(NH_4)_2SO_4$ (168356, Merck) solution used as the hydration buffer. To form an $H^+$ proton gradient for the loading of H33342, the liposome solution was dialyzed against 2 changes of saline solution (0.15 M NaCl) at 2 and 4 hours and then left to dialyze overnight at 4° C. H33342 was dissolved in saline and added to the liposome solution at a ratio of 10:1 (mol lipid:mol H33342) and incubated in an oven at 70° C. for 2 hours. The liposome solution was passed through a HiTrap desalting column with PBS to remove unencapsulated H33342. Fractions with a signal/background ratio of >100 were pooled together and stored at 4° C.

Visualization of hemolytic colonies: Assay medium was prepared by mixing BHI, fetal bovine serum (FBS), agarose and purified H33342 liposomes in the following quantities in a final volume of 100 ul: 1× BHI, 10% FBS (v/v), 1% (w/v) agarose, 4 ul H33342 liposomes. Thawed cultures ($10^2$-$10^3$ CFU) were added this assay medium and this mixture was then vortexed and spun briefly to reconsolidate the mixture. 70 μl of this mixture was pipetted onto a concave slide and a cover slip was placed on top of it. The samples were then incubated overnight in a humidified chamber at 37° C. Colonies were visualized at 10× magnification on a Zeiss Axiovert 200M microscope. For fluorescence visualization, colonies were excited with UV light (365 nm) and the emission (LP at 395 nm) was captured with a CoolSnap HQ CCD camera. Quantitative analysis of fluorescence images in FIG. 1D was performed using FIJI [22]. The images were firstly stacked together and a fixed area was defined in the colony to measure the mean of the intensity. Background readings were obtained by using the same defined dimensions to measure the fluorescence intensity outside the colony. The signal/background ratio was calculated by taking the mean intensity of the area in the colony divided by the mean intensity of the background. Four colonies were selected from every experiment. These steps were performed for every time point in time lapse experiments where relevant. For visualization of co-cultured beta-hemolytic S. pyogenes or S. aureus with alpha-hemolytic S. pneumoniae colonies, the procedure was similar as above except colonies were probed with anti-S. pneumoniae antibodies to identify S. pneumoniae colonies. Briefly, after incubation, the cover slip was removed, and the gel was washed once with 1× PBS pH 7.4. Next, the gel was blocked with 5% bovine serum albumin (BSA, A4503, Sigma-Aldrich) for three hours and probed with mouse anti-S. pneumoniae (1:50, 8437-5208, AbD Serotec) overnight. The antibodies were removed, washed thrice with 1× PBS pH 7.4 for one hour and then probed again with an Alexa Fluor 488 conjugated goat anti-mouse antibody (1:200, A11029, Life Technologies) overnight. The secondary antibodies were removed and washed thrice with 1× PBS pH 7.4 for one hour. All washing and probing steps were done in a humidified chamber at room temperature. Colonies were visualized with a 5× magnification lens on a Zeiss Axiovert 200M microscope. For fluorescence visualization, colonies were excited with UV or blue light (365 nm or 488 nm) and the emission (BP 445/50 nm, BP 525/50 nm) was captured using a CoolSnap HQ CCD camera.

All experiments above were carried out with the same exposure time with respect to the experiment and repeated three times.

Image processing and pattern recognition: For the detection of colonies in images, we applied a top-hat transform for background subtraction followed by thresholding using Otsu's method. Morphological opening was used to remove small blobs after thresholding. Next, the marker-controlled watershed algorithm was employed to separate the overlapping objects in the image. Finally, the connected component labelling algorithm was utilized to extract the foreground objects and background pixels.

To build the feature dataset for classification purpose, we measured the fluorescence intensity of a fixed circular area (radius: 20 pixels) from the centroid of the colony. If colonies were too small to accommodate a 20-pixel radius, a radius of 5 was used instead. The average of these intensities is referred to as 'colony fluorescence' in the main text. Further, the background intensity refers to the average of the background pixels.

A textural analysis was also performed by extracting the Gray-Level Co-occurrence Matrix (GLCM). The co-occurrence matrix provides the probability that a pixel with the intensity value i occurs at a predefined distance and direction with another pixel of intensity value j. This joint probability density function $P_{d,\theta}(i, j)$ can be used to extract the image textural features. In this work, we estimated the co-occurrence matrices for a distance of d=1 pixel in horizontal, vertical and diagonal directions (0, 45, 90 and 135). These matrices were obtained using a computational window size of 20 pixels in an 8-bit quantized image. The average of the four co-occurrence matrices results in the non-directional GLCM. We used this non-directional GLCM to extract the dissimilarity texture feature, which is similar to contrast but the weights increase linearly. It is given as:

$$\sum_{i,j=0}^{N-1} P(i, j)|i - j|$$

where N refers to the number of levels specified for quantization.

The support vector machine (SVM) classifier with linear kernel was used to classify beta-hemolytic and non-beta hemolytic organisms from admixture samples. Ten-fold stratified cross-validation was performed to determine classification performance.

The algorithm was implemented in Python 2.7.3. Morphological operations for colony detection and calculation of image features (intensity and dissimilarity) were carried out using scikit-image 0.10.0 module. SVM as implemented in the scikit-learn 0.15.0 module was used.

Uptake of free H33342 by bacteria: The uptake of free H33342 was investigated by repeating the experiment as above but replacing liposomal H33342 with free H33342 dye (final concentration, 160 nM). Sodium hexametaphosphate (305553, Sigma-Aldrich) was added to a concentration of up to 0.3% for membrane permeabilization experiments.

Liposome pull down assay: Frozen S. pyogenes and B. cereus cultures were inoculated into 25 ml of BHI media and incubated overnight at 37° C. The samples were then centrifuged at 3,900 g for 10 min. 20 ml of supernatant were collected and concentrated by centrifugation in spin columns at 3,900 g for 10 mins. This was repeated once. Next, phosphate buffered saline (PBS) was added to the concentrate to a final volume of 1.5 ml for both samples. 40 µl of SRB liposomes were added to 900 µl of the concentrate and continuously inverted at 37° C. for 1 hr. This solution was then centrifuged at 16000 g for 30 min, washed with 1 ml of 1× PBS and centrifuged at the same speed again. 960 µl of supernatant was then removed and the pellet was dissolved in the remaining wash solution by light vortexing. The samples were separated by a 10% Bis Tris gel 1.0 mm×12 well (NP0302-Box, Life Technologies) running in 1× MOPS buffer (NP0001, Life Technologies).

For visualization of protein bands, the gel was stained according to the Colloidal Coomassie protocol [23]. Briefly, the gel was fixed in 30% Ethanol+2% phosphoric acid for 1 hr and stained overnight with shaking. The stain was then disposed of, and the gel was washed thrice in ultrapure water, each lasting 10 min. Bands were excised with a scalpel. In-gel reduction, alkylation and digestion were performed with Montage In-Gel digestion ziptip kit (LSKG DZT 96, Millipore) according to manufacturer instructions.

Nano LC-ESI-MS: Separation of the digested peptides was carried out on an Eksigent nanoLC Ultra and ChiPLC-nanoflex (Eksigent, Dublin, Calif.) in Trap Elute configuration. A volume of 5-10 µl of the sample was loaded on a 200 µm×0.5 mm trap column and eluted on an analytical 75 µm×150 mm column. Both trap and analytical columns are made of ChromXP C18-CL, 3 µm (Eksigent, Germany). Peptides were separated by a gradient formed by 2% acetonitrile (ACN), 0.1% formic acid (FA) (mobile phase A) and 98% ACN, 0.1% FA (mobile phase B): 5%-12% of mobile phase B (20 min), 12%-30% of mobile phase B (90 min), 30%-90% of mobile phase B (2 min), 90% of mobile phase B (5 min), 90%-5% of mobile phase B (3 min), and 5%-5% of mobile phase B (13 min), at a flow rate of 300 nl/min. The MS analysis was performed on a TripleTOF 5600 system (AB SCIEX, Foster City, Calif., USA) in Information Dependent Mode. MS spectra was acquired using the Analyst 1.6 software (AB SCIEX) across the mass range of 400-1250 m/z in high resolution mode (>30000) with 250 ms accumulation time per spectrum. A maximum of 20 precursors per cycle was chosen for fragmentation from each MS spectrum with 100 ms minimum accumulation time for each precursor and dynamic exclusion for 15 s with charge state between 2 to 4. Tandem mass spectra will be recorded in high sensitivity mode (resolution>15000).

Protein Identification with ProteinPilot™ software: LC-MS/MS data (.wiff and .scan files) was transferred to ProteinPilot™ 4.0 (AB SCIEX) for processing and database searches. The database used was taken from UnitProt database of all proteins in S. pyogenes and B. cereus. The search parameters used were set as follows: Cysteine alkylation with MMTS; Trypsin Digestion; TripleTOF 5600; Biological modifications (All the protein modifications available in the ProteinPilot™ search engine are taken into consideration, which included most if not all the known protein modifications). Redundancy was eliminated by the grouping of identified proteins using the ProGroup algorithm in the software. A decoy database search strategy was used to determine the false discovery rate (FDR) for protein identification. A corresponding randomized database was generated using the Proteomics System Performance Evaluation Pipeline feature in the ProteinPilot™ Software 4.5. A cut-off threshold with 1% global FDR was applied for protein identification.

H33342 liposome leakage assay: H33342 liposomes were added to media (10% FBS in 1× BHI) and incubated at 37° C. The mixture was pipetted into a 384 well black plate at specific time points. Triton X-100 (final concentration 0.2%) was added to lyse the liposomes to find the maximum fluorescence (F100%) value of H33342 in the well.

The stability of the liposomes at time t was defined by the following formula:

$$\% \text{ Leakage} = \frac{F_t - F_{0\%}}{F_{100\%} - F_{0\%}} \times 100\%$$

where $F_t$ was the fluorescence reading at a specific time point, $F_{0\%}$ was the reading at $T_0$ when the liposomes were first added to the mixture and $F_{100\%}$ was the reading at $T_0$ when Triton X-100 was added to the mixture. The experiment was conducted three times and each time point in triplicates.

Fluorescent plate reading assay: Dilutions of frozen bacterial stocks in PBS were inoculated with SRB liposomes, BHI (BD Bacto) and FBS in a total volume of 50 µl in a 384 well black plates (781091, Greiner). An adhesive clear plastic seal (Z369667, Sigma-Aldrich) was placed over the plate to prevent evaporation over the course of the experiment. The assay was carried out in a Tecan M200 Pro plate reader (Tecan Group Ltd). The excitation and emission was set to 526/584, with a gain of 70. Absorbance readings ($OD_{600}$) were also monitored for confirmation of bacterial growth in the wells. The plate was continuously measured at 37° C. every ten minutes for fifteen hours. Colony forming units (CFUs) were determined by plating the dilutions used in the assay and counting the number of colonies formed after overnight incubation. L-SRB lysis was calculated by the following formula:

$$\% \text{ Lysis} = \frac{F_t - F_{0\%}}{F_{100\%} - F_{0\%}} \times 100\%$$

where $F_t$ is the fluorescence reading at a specific time point, $F_{0\%}$ is the average of four blank wells filled with media+L-SRB but no Triton X-100 and bacteria, and $F_{100\%}$ is the average of four blank wells with Triton X-100 added. The experiment was conducted three times and each time point in four replicates.

Admixture experiments were conducted similarly as above except the experiment was stopped at twelve hours.

Immuno-fluorescence labelling of cells in 384 well plates: Cells from four wells were collected, washed once in 1× PBS pH 7.4 and normalized to a fixed number before heat fixing on glass slides. The cells were fixed again with 10% Neutral Buffered Formalin (HT501128, Sigma-Aldrich) for 10 minutes and washed thrice in 1× PBS pH 7.4. Next, fixed cells were blocked with 5% BSA in PBS for 1 hour, washed thrice in 1× PBS pH 7.4 and probed with FITC conjugated mouse anti-S. pneumoniae antibody (1:50, ab35165, Abcam)

for 1 hour. The cells were washed again in 1× PBS pH7.4 and mounted with Fluoromount (F4680, Sigma-Aldrich). The cells were imaged on the same day using a Zeiss Axiovert 200M microscope. For fluorescence visualization, cells were excited with blue light (488 nm) and the emission (BP 525/50 nm) was captured on a CoolSnap HQ CCD camera.

Statistical analysis: We used a two tailed Mann Whitney test for the comparison of nonparametric independent samples in Graphpad Prism 5. A single tailed T-test was used for the comparison of hemolytic bacteria to alpha hemolytic S. pneumoniae. These values were computed in Microsoft Excel 2007 and used to generate TTD curves.

Example 2

Liposomes as Blood Substitutes

RBC agar exhibits a clearing around beta-hemolytic colonies. This clearing, which is caused by the lysis of RBCs around of the colony, is known to be mediated by phospholipases and pore formers secreted by the microorganism. Since liposomes have traditionally been used as models for membrane research, we postulated that beta-hemolytic bacteria which lyse erythrocytes would also be able to lyse liposomes. In essence, the hypothesis that liposomes would be a direct replacement for erythrocytes in RBC agar was tested.

Figure 2:
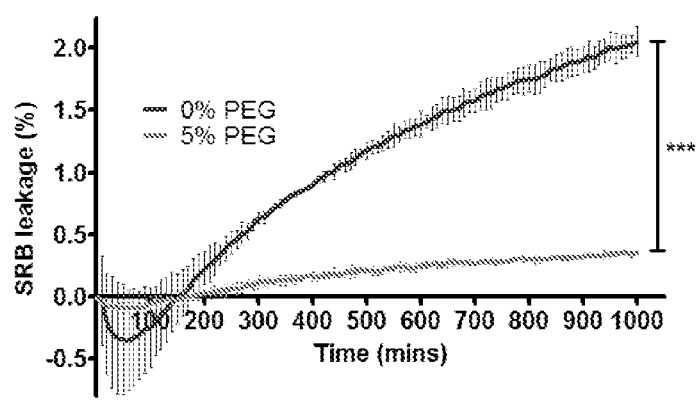
FIG. 2 shows liposomal stability in growth media. The omission of DSPE-PEG$_{2000}$ from L-SRB significantly increases the amount of Sulforhodamine B (SRB) leakage from the liposomes. Experiments were repeated at least thrice. Error bar summaries of the data are means±s.d. ***P<0.0001.

The liposomal substitute for RBCs had to be optically transparent, cost effective to produce, stable when suspended in rich growth media, resistant to alpha-hemolysis and easily detected when lysed. To meet these criteria, liposomes were formulated at the nanoscale using PEGylation for steric-stabilization [7] and saturated phosphatidylcholine coupled with high cholesterol content to decrease membrane permeability [8]. As for detection, fluorescent dyes exhibit self-quenching when encapsulated at high concentrations within the internal aqueous liposomal compartment. This phenomenon was exploited to create two types of liposomes; liposomal Hoechst 33342 (L-Hoechst) and liposomal Sulforhodamine B (L-SRB). Upon disruption of the liposomes by physical or chemical means, these dyes are de-quenched by release, producing a signal many times above their encapsulated fluorescence. Emphasizing the importance of PEG for stability, it was found that PEGylated L-SRB liposomes leaked 0.2% of their contents over 16.7 hours whereas the non-PEGylated version leaked more than 5.8 times that amount within the same period (FIG. 2).

Example 3

Liposomal H33342 Detects Beta-Hemolytic Micro-Colonies in Agar

Both Sulforhodamine B and Hoechst 33342 (H33342) have very different physicochemical properties. At physiological pH, SRB is ineffective for visualizing hemolytic bacterial colonies because it is hydrophilic and thus unable to penetrate bacterial cell membranes. In contrast, H33342 is an amphiphilic, membrane-permeable nuclear stain which would hypothetically be ideal for colony visualization.

Figure 3A:
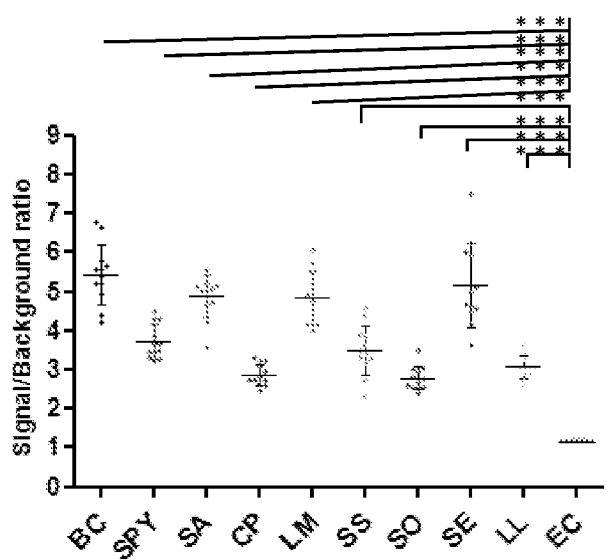
FIGS. 3A-3C show studies with H33342.
Figure 3B:
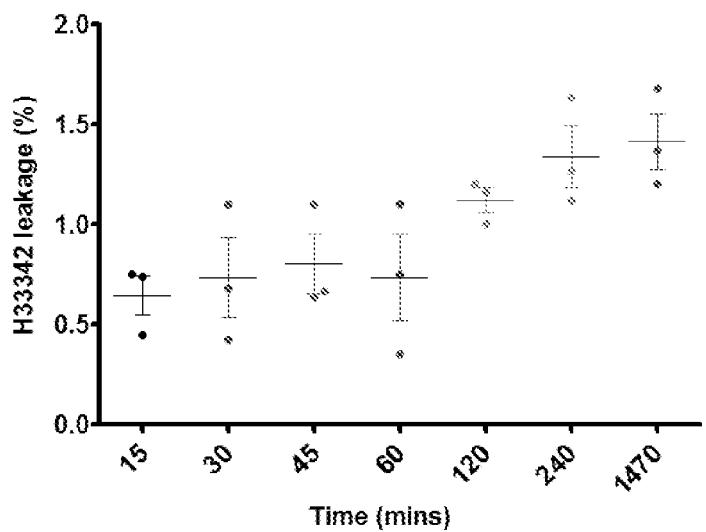

First, the ability of bacterial colonies to be associated with H33342 was tested by culturing a variety of bacteria on BHI agar with a non-lethal concentration of 160 nM H33342 (FIG. 3A). Interestingly, gram-positive bacteria but not gram-negative bacteria were observed to fluoresce blue. On one hand, this result showed that H33342, once released from its highly stable encapsulated form (FIG. 3B) would be assimilated by gram-positive beta-hemolytic colonies to create a non-diffusible signal (FIG. 3B). On the other hand, the results also suggested that H33342 would not be a suitable indicator for beta-hemolytic gram negative colonies.

Figure 3C:
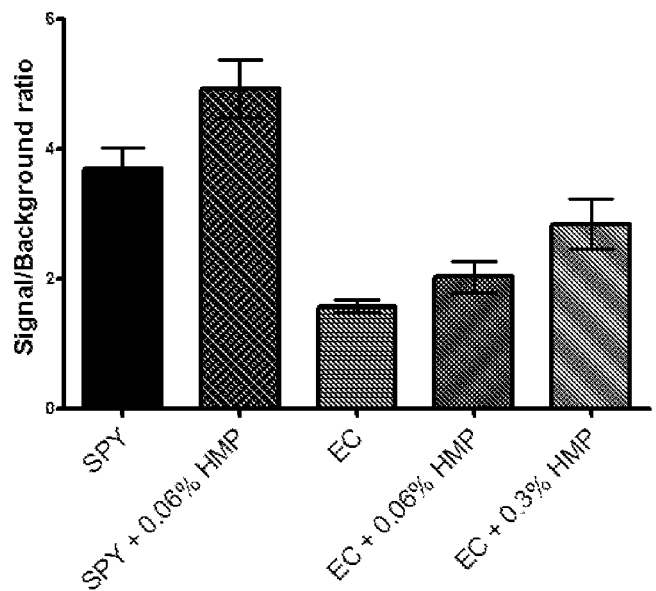

One possible explanation was that gram-negative bacteria in particular have limited permeability to H33342[9]. We decided to test the idea that sodium hexametaphosphate, a cell-wall permeabilizing agent, would improve the permeability of gram-negative bacteria to H33342. We observed that cell-wall permeabilization did indeed increase the colony fluorescence of E. coli but the concentrations of sodium hexametaphosphate required to increase E. coli colony fluorescence by a mere 80% turned out to be lethal to the gram-positive bacterium S. pyogenes (FIG. 3C). For this reason, the L-Hoechst experiments were focused on gram-positive bacteria, using the gram-negative E. coli only as a control for colony fluorescence.

To retain H33342 despite its ability to traverse bilayers, the liposomal interior was acidified relative to the exterior [10] so that H33342 diffusing into a liposome would become preferentially charged and hence liposomally entrapped. This principle was used to remotely load L-Hoechst with high concentrations of the dye. Various bacterial strains (Table 1) were then inoculated in Brain Heart Infusion (BHI) agar media admixed with L-Hoescht and incubated on concave well slides for microscopic visualization. After overnight incubation, colonies of all five beta-hemolytic bacteria tested (B. cereus, S. pyogenes, S. aureus, C. perfringens and L. monocytogenes) turned fluorescent. In contrast, colonies of the alpha- or gamma-hemolytic bacteria used as controls remained low in fluorescence (FIG. 1A). Colony fluorescence quantified as a measure of beta-hemolytic activity was able to perfectly separate beta-hemolysis from controls (FIG. 1B). In the worst case comparison, the weakest beta-hemolysis from L. monocytogenes was 2-fold above the highest background signal from Lactococcus lactis. In the best case, the strongest beta-hemolysis from S. pyogenes was 30-fold above E. coli XL1 which had the lowest background fluorescence. L. monocytogenes which is often described as "subtly" hemolytic and difficult to identify on regular blood agar was easily distinguishable from control microbes in the liposomal assay.

Figure 1D:
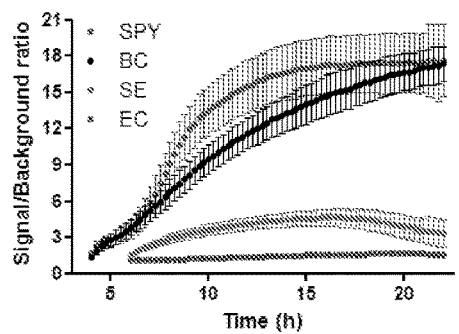
Figure 1E:
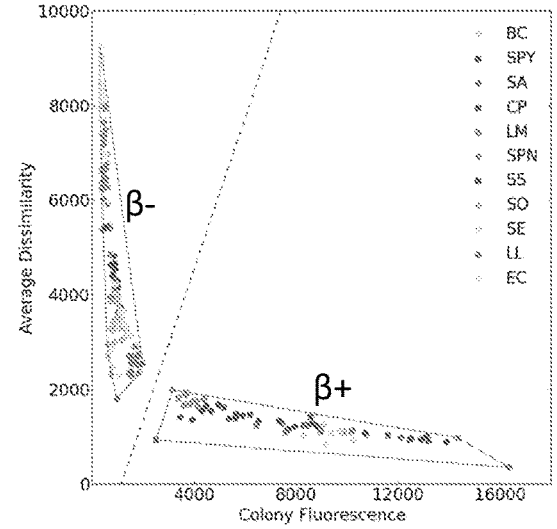

Interestingly, it was noticed that colony fluorescence associated with beta-hemolysis was qualitatively different from background fluorescence associated with control bacteria. Specifically, the first looked uniform whereas the second had a granular texture. To quantitate this textural component, the Dissimilarity parameter using the Grey Level Co-occurrence Matrix (GLCM) of the fluorescent micro-colonies was computed. Consistent with visual intuition, beta-hemolysis was found to be inversely proportional to Dissimilarity, hence creating a second complementary axis to separate beta-hemolysis from controls (FIG. 1E).

To study the kinetics of beta-hemolytic activity, individual colonies of B. cereus, S. pyogenes, Staphylococcus epidermidis and E. coli DH5α were imaged at 15 minute intervals. The fluorescence of B. cereus and S. pyogenes colonies both exhibited a sharp exponential increase after a 5 hour lag, reaching similar fluorescence levels after 24 hours (FIG. 1D). Non-hemolytic colonies also gained fluorescence at a basal level, likely due to the uptake of trace amounts of un-encapsulated H33342. All bacterial colonies reached maximum fluorescence when they plateaued in colony size.

Example 4

Beta-Hemolytic Colonies can be Distinguished in Admixtures

Real world scenarios involve bacterial populations in coexistence. We were curious to see if S. pyogenes and S. aureus, both common beta-hemolytic human pathogens, could be told apart from S. pneumoniae, a strongly alpha-hemolytic commensal often intermixed with them. After co-culture on BHI agar with L-Hoechst, S. pneumoniae colonies were immunostained with green fluorescence, allowing us to tell them apart from S. pyogenes or S. aureus. As expected, S. pyogenes and S. aureus were fluorescently labelled blue from lysis of L-Hoechst whereas S. pneumoniae showed no lysis (FIG. 4A). Similar to our prior experiments using GLCM, we found that the Dissimilarity parameter was also applicable to admixtures and could be used to distinguish S. pyogenes and S. aureus from S. pneumoniae in BHI agar co-culture (FIGS. 4B-4D).

Example 5

Detection of Hemolytic Bacteria in 384 Well Plates

Curious to see if beta-haemolytic bacteria could similarly be detected in broth, pure populations of various bacteria were inoculated into BHI broth with L-SRB. L-SRB was used instead of L-Hoechst because auto-fluorescence from BHI media coincides with H33342's emission range. When normalized to the fluorescence signal from 100% lysed L-SRB, alpha- and gamma-hemolytic bacteria lysed only up to 0.5% of L-SRB despite highly turbid growth (FIG. 5G; FIGS. 6A-6D). In contrast, beta-hemolytic bacteria lysed 10-65% of L-SRB, resulting in signal levels 26-125 times above S. pneumoniae. Importantly, L-SRB lysis by C. perfringens could be robustly detected when Oxyrase was added to create an anoxic environment, demonstrating that L-SRB can detect beta-hemolytic obligate anaerobes.

To ascertain the limit of detection, the above experiment were repeated with serial dilutions of each individual bacterium. As expected, the inflexion point when each bacterium hit exponential growth increased monotonically with the number of CFUs inoculated (FIGS. 5A-5F and FIG. 5I). Importantly, detect beta-hemolysis could be detected in wells with 1-10 CFUs, showing that this assay is sensitive at limiting dilutions. Time-To-Detection (TTD) was defined as the point when the fluorescence of a time-series significantly exceeded that of S. pneumoniae at $p<0.005$. This principle is illustrated for S. pyogenes where TTDs for each time-series is marked by an asterisk (FIG. 5B). We also observed a strong linear correlation ($R^2>0.9$) between TTD and inoculum size for all beta-hemolytic bacteria (FIG. 5H), showing that if a bacterial identity is known, TTD can be a quantitative indicator of inoculum size. TTD was found to range approximately from 1-5 hours for $10^4$ cells and 8-15 hours for single cells. TTD was not significantly affected by the status of the cell; frozen and live BC cells had similar TTDs except in low concentrations of B. cereus cells (FIGS. 7A-7D).

Figure 8A:
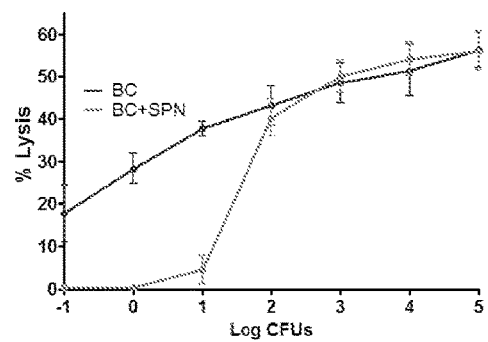
FIGS. 8A-8D show that the TTD in broth for BC beta-hemolysis is unaffected by admixing with up to a 100-fold excess of alpha-hemolytic SPN. BC was either incubated alone or co-incubated with $10^4$ SPN cells over 12 hours in a 384 well plate. All values in this figure are based on the mean of 3 independent experiments each with 4 replicates.
Figure 8B:
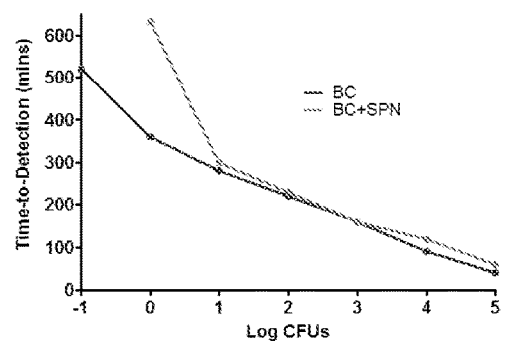
Figure 8C:
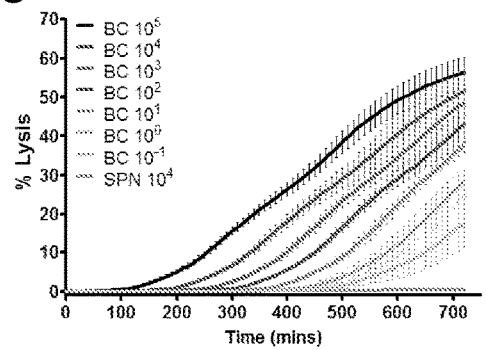
Figure 8D:
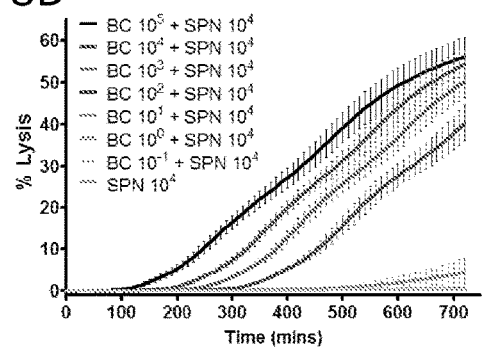
Figure 9:
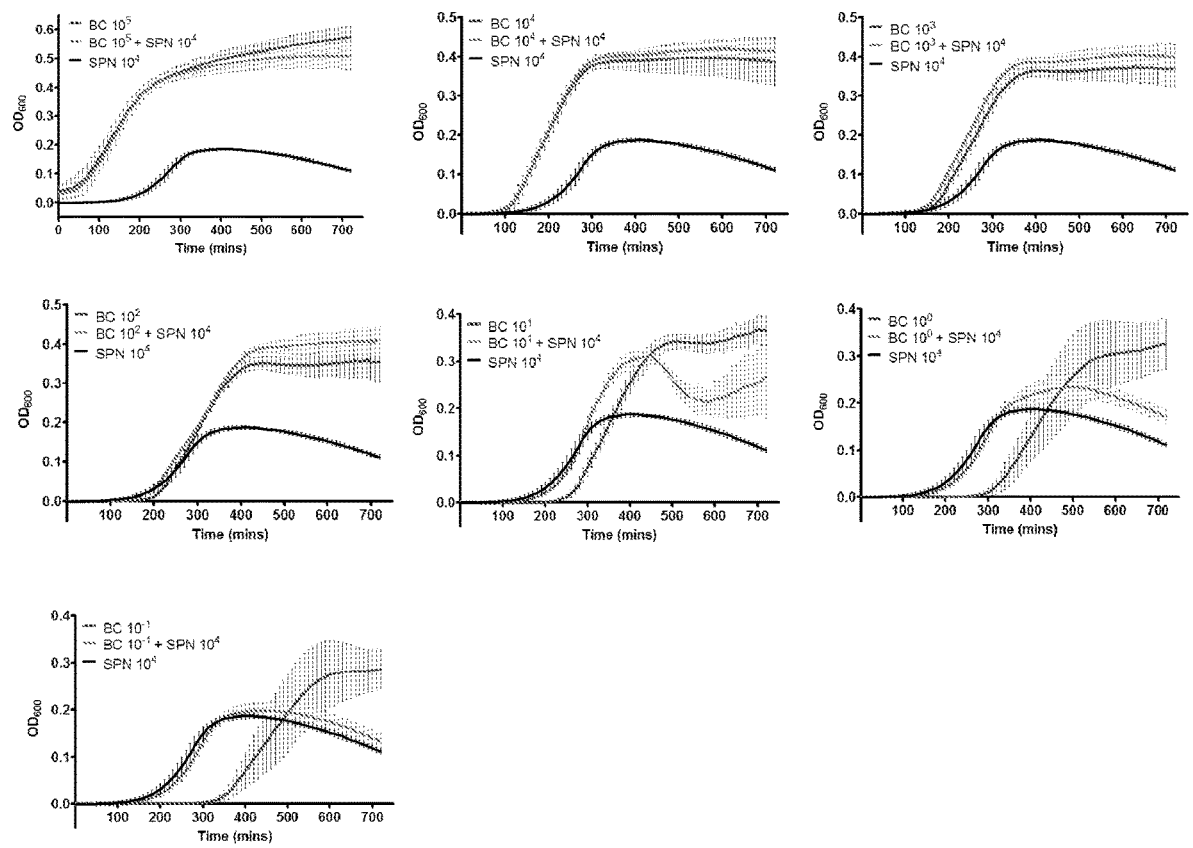
Figure 10:
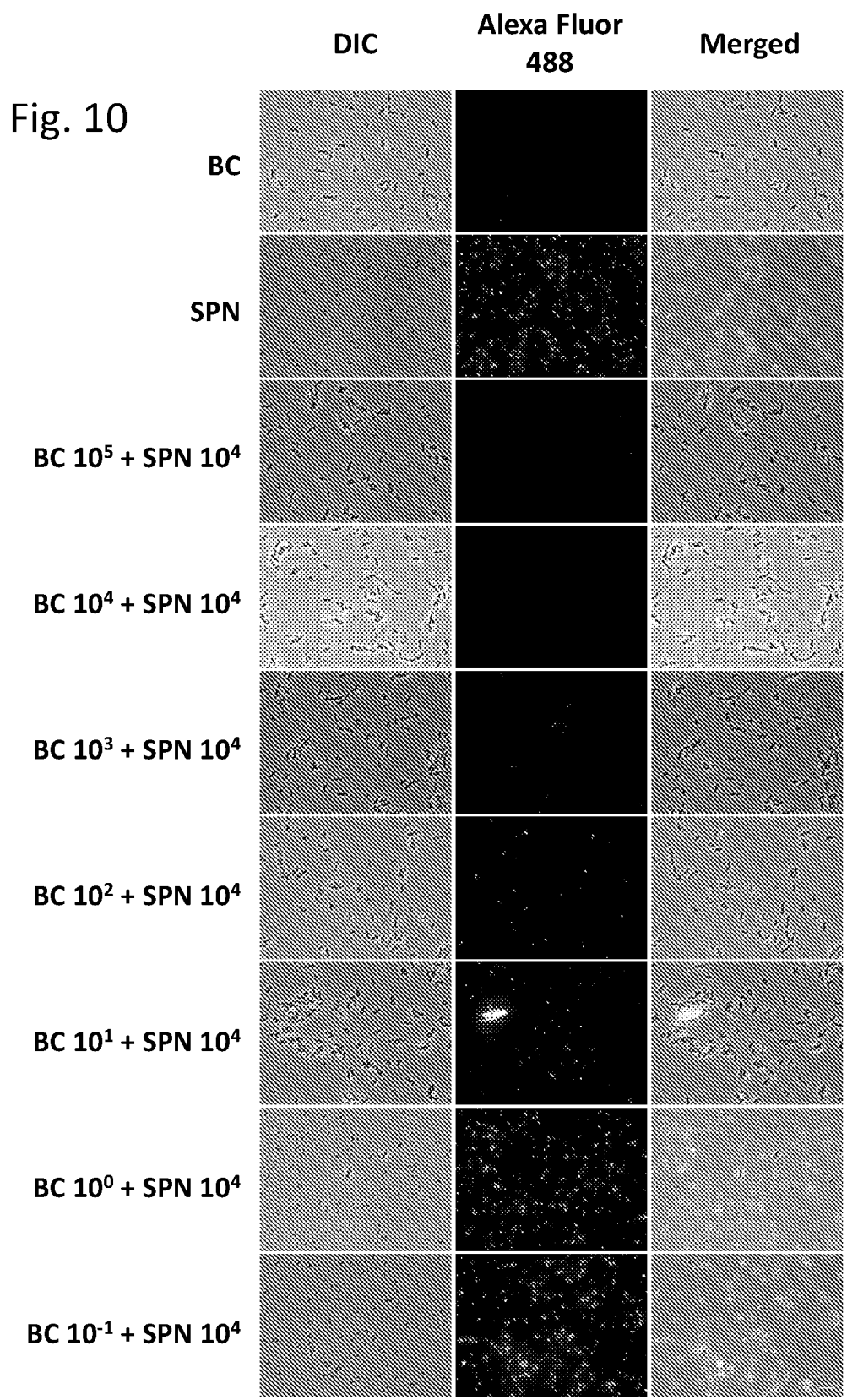

In many scenarios, beta-hemolytic bacteria are heavily outnumbered by alpha- and gamma-hemolytic commensal bacteria. To study how the limit of detection is affected by admixing, a variable quantity of B. cereus together with a fixed quantity ($10^4$ CFUs) of S. pneumoniae was inoculated. There was practically no difference to TTD as long as there were at least 10 CFUs of B. cereus (FIG. 8A). TTD was only affected in wells with near limiting dilutions of 1-10 B. cereus CFUs (FIG. 8B). At these dilutions, S. pneumoniae enter exponential growth earlier hence outcompeting B. cereus growth (FIGS. 9 and 10).

Example 6

Bacterial Membrane Interacting Proteins Co-Purify with Liposomes

It was desired to test the idea that beta-hemolytic agents act directly on liposomal bilayers to lyse and release their contents. One way to corroborate this hypothesis is to examine if liposomes incubated with media conditioned with the growth of beta-hemolytic microorganisms would physically associate and hence enrich for beta-hemolysins. First, liposomes were incubated in S. pyogenes conditioned media. Liposomes purified through ultracentrifugation were found to co-pellet with Streptolysin O, a canonical example of a beta-haemolysin (FIGS. 5A and 5B). Four other proteins, oligopeptide binding proteins, ATP synthase, Elongation Factor Tu and a putative secreted protein were also identified. These proteins are known to associate or localize in membranes [11-13]. We repeated the experiment using B. cereus conditioned media and found similarly that the liposomes co-purified with the well-characterized membrane interacting proteins Alveolysin [14], Hemolytic Enterotoxin and Enterotoxin B [15]. These observations support the idea that liposomes are directly lysed by hemolysins secreted by bacteria and are hence suitable agents for detecting beta-hemolysis.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Pichichero, M. E. Group A streptococcal tonsillopharyngitis: cost-effective diagnosis and treatment. *Annals of emergency medicine* 25, 390-403 (1995).
2. Gerber, M. A. & Shulman, S. T. Rapid diagnosis of pharyngitis caused by group A streptococci. *Clinical microbiology reviews* 17, 571-580 (2004).
3. Needham, C. A., McPherson, K. A. & Webb, K. H. Streptococcal pharyngitis: impact of a high-sensitivity antigen test on physician outcome. *Journal of clinical microbiology* 36, 3468-3473 (1998).
4. Chen, C. C., Teng, L. J. & Chang, T. C. Identification of clinically relevant viridans group streptococci by sequence analysis of the 16S-23S ribosomal DNA spacer region. *Journal of clinical microbiology* 42, 2651-2657 (2004).
5. Suo, B. et al. Development of an oligonucleotide-based microarray to detect multiple foodborne pathogens. *Molecular and cellular probes* 24, 77-86 (2010).
6. Henry, B. D. et al. Engineered liposomes sequester bacterial exotoxins and protect from severe invasive infections in mice. *Nature biotechnology* 33, 81-88 (2015).
7. Basáñez, G., Goñi, F. M. & Alonso, A. Poly (ethylene glycol)-lipid conjugates inhibit phospholipase C-induced lipid hydrolysis, liposome aggregation and fusion through independent mechanisms. *FEBS letters* 411, 281-286 (1997).
8. De Gier, J., Mandersloot, J. & Van Deenen, L. Lipid composition and permeability of liposomes. *Biochimica et Biophysica Acta (BBA)-Biomembranes* 150, 666-675 (1968).
9. Vaara, M. Agents that increase the permeability of the outer membrane. *Microbiological reviews* 56, 395-411 (1992).
10. Haran, G., Cohen, R., Bar, L. K. & Barenholz, Y. Transmembrane ammonium sulfate gradients in liposomes produce efficient and stable entrapment of amphipathic weak bases. *Biochimica et Biophysica Acta (BBA)-Biomembranes* 1151, 201-215 (1993).
11. Monnet, V. Bacterial oligopeptide-binding proteins. *Cellular and Molecular Life Sciences CMLS* 60, 2100-2114 (2003).
12. Severin, A. et al. Proteomic analysis and identification of *Streptococcus pyogenes* surface-associated proteins. *Journal of bacteriology* 189, 1514-1522 (2007).
13. Yoshida, M., Muneyuki, E. & Hisabori, T. ATP synthase—a marvellous rotary engine of the cell. *Nature Reviews Molecular Cell Biology* 2, 669-677 (2001).
14. Geoffroy, C., Mengaud, J., Alouf, J. & Cossart, P. Alveolysin, the thiol-activated toxin of *Bacillus alvei*, is homologous to listeriolysin O, perfringolysin O, pneumolysin, and streptolysin O and contains a single cysteine. *Journal of bacteriology* 172, 7301-7305 (1990).
15. Lindbäck, T. et al. Cytotoxicity of the *Bacillus cereus* Nhe enterotoxin requires specific binding order of its three exoprotein components. *Infection and immunity* 78, 3813-3821 (2010).
16. Kim, H. J., Bennetto, H. P., Halablab, M. A., Choi, C. & Yoon, S. Performance of an electrochemical sensor with different types of liposomal mediators for the detection of hemolytic bacteria. *Sensors and Actuators B: Chemical* 119, 143-149 (2006).
17. Silbert, L. et al. Rapid chromatic detection of bacteria by use of a new biomimetic polymer sensor. *Applied and environmental microbiology* 72, 7339-7344 (2006).
18. Thet, N. et al. Visible, colorimetric discrimination between pathogenic strains of *Staphylococcus aureus* and *Pseudomonas aeruginosa* using fluorescent dye containing lipid vesicles. *Biosensors and Bioelectronics* 41, 538-543 (2013).
19. Food & Administration, D. Bad Bug Book, Foodborne Pathogenic Microorganisms and Natural Toxins. Second Edition. (2012).
20. Brynestad, S. & Granum, P. E. *Clostridium perfringens* and foodborne infections. *International journal of food microbiology* 74, 195-202 (2002).
21. Fratamico, J. L. P. M. Bhunia A. K. & Smith *Foodborne pathogens: microbiology and molecular biology*. (Caister Academic Press, Wymondham, Norofolk, UK.: 2008).
22. Schindelin, J. et al. Fiji: an open-source platform for biological-image analysis. *Nature Methods* 9, 676-682 (2012).
23. Dyballa N & Metzger S. Fast and sensitive coomassie staining in quantitative proteomics. *Methods in Molecular Biology* 893, 47-59 (2009).

What is claimed is:

1. A kit for detecting the presence of a beta-hemolytic pathogen in a sample, the kit comprising sterically-stabilized liposomes and a fluorophore, wherein the sterically-stabilized liposomes are lysed by a beta-hemolytic pathogen and are not lysed by an alpha-hemolytic pathogen or by a gamma-hemolytic pathogen;

wherein the sterically-stabilized liposomes are prepared from a mixture of:
   (1) a membrane forming phospholipid selected from the group consisting of (a) a saturated phosphatidylcholine and (b) a synthetic phosphatidylcholine with saturated fatty acid tails selected from the group consisting of dimyristoyl-phosphatidylcholine, dipalmitoyl-phosphatidylcholine, and distearoyl-phosphatidylcholine;
   (2) cholesterol; and
   (3) a conjugate of polyethylene glycol (PEG), wherein the PEG has a molecular weight from 1,000 to 5,000, and wherein the PEG is conjugated to a molecule selected from the group consisting of distearoyl phosphatidylethanolamine (DSPE), dipalmitoyl phosphatidylethanolamine (DPPE) and dimyristoyl phosphatidylethanolamine (DMPE);

wherein the molar ratio of (1):(2) is in the range of 2:1 to 1:1 and (3) is present at 5% (mol/mol); and wherein the fluorophore is separate from the sterically-stabilized liposomes and is encapsulated into said liposomes for detecting the presence of the beta-hemolytic pathogen in the sample.

2. The kit of claim 1, wherein the kit further comprises a growth medium.

3. The kit of claim 2, wherein the growth medium is a solid growth medium.

4. The kit of claim 3, wherein the solid medium comprises brain heart infusion (BHI), fetal bovine serum (FBS) and agarose.

5. The kit of claim 3, wherein the fluorophore is Hoechst 33342 (H33342).

6. The kit of claim 2, wherein the growth medium is a liquid growth medium.

7. The kit of claim 6, wherein the liquid growth medium comprises brain heart infusion (BHI), fetal bovine serum (FBS) and an antioxidant.

8. The kit of claim 6, wherein the fluorophore is sulforhodamine B (SRB).

9. The kit of claim 1, wherein the kit further comprises a control pathogen.

10. The kit of claim 1, wherein the sterically-stabilized liposomes are prepared from a mixture of (1) hydrogenated egg yolk phosphatidylcholine (HEPC), (2) cholesterol and (3) distearoyl phosphatidylethanolamine (DSPE)-PEG2000 in a molar ratio of (1):(2):(3) of 50:45:5.

11. A composition for detecting the presence of a beta-hemolytic pathogen in a sample comprising sterically-stabilized liposomes comprising an encapsulated fluorophore, wherein the sterically-stabilized liposomes are lysed by a beta-hemolytic pathogen and are not lysed by an alpha-hemolytic pathogen or by a gamma-hemolytic pathogen;

wherein the sterically-stabilized liposomes are prepared from a mixture of:
(1) a membrane forming phospholipid selected from the group consisting of (a) a saturated phosphatidylcholine and (b) a synthetic phosphatidylcholine with saturated fatty acid tails selected from the group consisting of dimyristoyl-phosphatidylcholine, dipalmitoyl-phosphatidylcholine, and distearoyl-phosphatidylcholine;
(2) cholesterol; and
(3) a conjugate of polyethylene glycol (PEG), wherein the PEG has a molecular weight from 1,000 to 5,000, and wherein the PEG is conjugated to a molecule selected from the group consisting of distearoyl phosphatidylethanolamine (DSPE), dipalmitoyl phosphatidylethanolamine (DPPE) and dimyristoyl phosphatidylethanolamine (DMPE);

wherein the molar ratio of (1):(2) is in the range of 2:1 to 1:1 and (3) is present at 5% (mol/mol).

12. The composition of claim 11, wherein the fluorophore is Hoechst 33342 (H33342).

13. The composition of claim 11, wherein the fluorophore is sulforhodamine B (SRB).

14. The composition of claim 11, wherein the sterically stabilized liposomes are prepared from a mixture of (1) hydrogenated egg yolk phosphatidylcholine (HEPC), (2) cholesterol and (3) distearoyl phosphatidylethanolamine (DSPE)-PEG2000 in a molar ratio of (1):(2):(3) of 50:45:5.

* * * * *